US010968153B2

(12) United States Patent
Sherwood

(10) Patent No.: US 10,968,153 B2
(45) Date of Patent: Apr. 6, 2021

(54) METHOD OF CONVERTING A BROMINATED HYDROCARBON TO A CHLORINATED HYDROCARBON

(71) Applicant: Eagle US 2 LLC, Houston, TX (US)

(72) Inventor: Scott A. Sherwood, Irwin, PA (US)

(73) Assignee: Eagle US 2 LLC, Houston, TX (US)

( * ) Notice: Subject to any disclaimer, the term of this patent is extended or adjusted under 35 U.S.C. 154(b) by 0 days.

(21) Appl. No.: 16/945,962

(22) Filed: Aug. 3, 2020

(65) Prior Publication Data

US 2021/0047250 A1 Feb. 18, 2021

Related U.S. Application Data

(60) Provisional application No. 62/886,383, filed on Aug. 14, 2019.

(51) Int. Cl.
*C07C 17/20* (2006.01)
*B01J 49/07* (2017.01)
(Continued)

(52) U.S. Cl.
CPC ............ *C07C 17/204* (2013.01); *B01J 41/14* (2013.01); *B01J 49/07* (2017.01); *C07C 17/275* (2013.01);
(Continued)

(58) Field of Classification Search
CPC ..... C07C 17/275; C07C 17/389; C07C 19/01; C07C 19/075; C07C 19/045; C07C 19/03;
(Continued)

(56) References Cited

U.S. PATENT DOCUMENTS 2,855,371 A 10/1958 Abrams
3,275,549 A 9/1966 Crabb et al.
(Continued)

FOREIGN PATENT DOCUMENTS

DE 249259 A1 9/1987
DE 287937 A5 3/1991
GB 1439271 6/1976

OTHER PUBLICATIONS

Aizenberg, et al., "New Approach for the Simple and Economic Preparation of Inorganic Bromide Salts", Ind. Eng. Chem. Res. 1992, pp. 431-434, vol. 31.
(Continued)

*Primary Examiner* — Jafar F Parsa
(74) *Attorney, Agent, or Firm* — The Webb Law Firm

(57) ABSTRACT

The present invention provides a method of converting a brominated hydrocarbon to a chlorinated hydrocarbon that involves contacting together the brominated hydrocarbon and a chlorinated ion exchange resin that has a water content of less than or equal to 30 percent by weight, based on the total weight of the chlorinated ion exchange resin and the water. The brominated hydrocarbon includes at least one replaceable bromo group, where each replaceable bromo group is independently covalently bonded to an $sp^3$ hybridized carbon. Contact between the brominated hydrocarbon and the chlorinated ion exchange resin results in replacement of at least one replaceable bromo group of the brominated hydrocarbon with a chloro group, and correspondingly conversion of at least a portion of the brominated hydrocarbon to the chlorinated hydrocarbon.

24 Claims, 3 Drawing Sheets

(51) Int. Cl.
- *B01J 41/14* (2006.01)
- *C07C 17/275* (2006.01)
- *C07C 19/045* (2006.01)
- *C07C 19/01* (2006.01)
- *C07C 19/075* (2006.01)
- *C07C 17/389* (2006.01)
- *C07C 19/03* (2006.01)

(52) U.S. Cl.
 CPC ............ *C07C 17/389* (2013.01); *C07C 19/01* (2013.01); *C07C 19/03* (2013.01); *C07C 19/045* (2013.01); *C07C 19/075* (2013.01)

(58) Field of Classification Search
 CPC ...... B01J 20/18; B01D 53/02; B01D 53/0423; B01D 2259/402; B01D 2253/1085
 See application file for complete search history.

(56) References Cited

U.S. PATENT DOCUMENTS

| | | | |
|---|---|---|---|
| 4,197,262 A | * | 4/1980 | Davis .................... C07C 17/204 570/254 |
| 4,517,751 A | | 5/1985 | Ross et al. |
| 2009/0184053 A1 | | 7/2009 | Mortimer et al. |

OTHER PUBLICATIONS

Borders, Jr., et al., "Synthesis of Sulfonyl Fluorides by Use of Fluoride Ion Exchange Resin", J. Org. Chem., 1972, pp. 3549-3550, vol. 37, No. 22.

Chiles, et al. "Preparation and Synthetic Utility of Phase-Transfer Catalysts Anchored to Polystyrene", Journal of Organic Chemistry, 1980, pp. 2915-2918, vol. 45, No. 14.

Dougherty, "Some Observations on the Catalytic Activity of Aluminum Chloride", J. Am. Chem. Soc., 1929, pp. 576-580, vol. 51, No. 2.

Li, et al., "Synthesis of pyridinium N-chloramines for antibacterial applications", Tetrahedron Letters, 2017, pp. 321-325, vol. 58.

Pollio, "Determination of Moisture in Ion Exchange Resins by Karl Fischer Reagent", Analytical Chemistry, 1963, pp. 2164-2165, vol. 35, No. 13.

Sharma, et al., "Determination of Water in Ion-Exchange Resins: Anion Exchange Resins", Analytical Chemistry, 1970, pp. 1287-1290, vol. 42, No. 11.

Urata, "Reaction of Halogen-Based Anion Exchange Resins with 1-Bromo-2-Chloroethane", Journal of the Chemical Society of Japan (Nippon Kagaku Zasshi), 1962, pp. 85-89 (1045-1049), vol. 83, No. 9.

\* cited by examiner

METHOD OF CONVERTING A BROMINATED HYDROCARBON TO A CHLORINATED HYDROCARBON

CROSS REFERENCE TO RELATED APPLICATION

The present application is entitled to and claims priority to U.S. Provisional Patent Application No. 62/886,383, filed on Aug. 14, 2019, the disclosure of which is incorporated herein by reference in its entirety.

FIELD OF THE INVENTION

The present invention relates to a method of converting a brominated hydrocarbon that includes at least one replaceable bromo group that is bonded to an $sp^3$ hybridized carbon, that involves contacting together the brominated hydrocarbon and an ion exchange resin that includes chloride groups, where the ion exchange resin has a water content of less than or equal to 30 percent by weight, based on the total weight of the ion exchange resin and the water, thereby converting at least a portion of the brominated hydrocarbon to chlorinated hydrocarbon, and isolating the chlorinated hydrocarbon from the ion exchange resin.

BACKGROUND OF THE INVENTION

Sources of chlorine are often contaminated with some bromine. The use of such bromine contaminated sources of chlorine in the preparation of chlorinated hydrocarbons typically results in the formation of undesirable co-product hydrocarbons that include bromo groups or a combination of both bromo groups and chloro groups bonded thereto. It can be difficult to separate the brominated hydrocarbon co-products from the target chlorinated hydrocarbon products. The brominated hydrocarbon co-products can, in some instances, be separated/isolated by distillation methods, such as fractional distillation. Further use or modification of the brominated hydrocarbon co-products is not usually feasible. Typically, the isolated brominated hydrocarbon co-products are incinerated. As a result, chlorine, such as in the form of hydrogen chloride, recovered from the incineration process is often contaminated with bromine materials, such as hydrogen bromide.

It would be desirable to develop new methods of reducing or eliminating the amount of brominated hydrocarbon co-products that are present with target chlorinated hydrocarbon products. It would be further desirable that such newly developed methods involve converting the brominated hydrocarbon co-products to chlorinated hydrocarbon products. It would be additionally desirable that the conversion of brominated hydrocarbon co-products to chlorinated hydrocarbon products have reduced or minimized waste streams associated therewith, and be economically reasonable to implement and conduct.

SUMMARY OF THE INVENTION

In accordance with the present invention, there is provided a method of converting a brominated hydrocarbon to a chlorinated hydrocarbon comprising: (a) providing the brominated hydrocarbon, wherein the brominated hydrocarbon comprises at least one replaceable bromo group, wherein each replaceable bromo group is independently covalently bonded to an $sp^3$ hybridized carbon; (b) contacting together the brominated hydrocarbon and an ion exchange resin comprising chloride groups, wherein the ion exchange resin comprises water in an amount of less than or equal to 30 percent by weight, based on the total weight of said ion exchange resin and the water, thereby replacing at least one replaceable bromo group of the brominated hydrocarbon with a chloro group, and converting at least a portion of the brominated hydrocarbon to the chlorinated hydrocarbon; and (c) isolating the chlorinated hydrocarbon from the ion exchange resin.

In further accordance with the present invention, there is also provided a method of converting a brominated hydrocarbon to a chlorinated hydrocarbon comprising: (a) providing a feed stream comprising the brominated hydrocarbon, wherein the brominated hydrocarbon comprises at least one replaceable bromo group, wherein each replaceable bromo group is independently covalently bonded to an $sp^3$ hybridized carbon; (b) providing a first fixed bed vessel comprising a first fixed bed comprising an ion exchange resin comprising chloride groups, wherein the ion exchange resin comprises water in an amount of less than or equal to 30 percent by weight, based on the total weight of said ion exchange resin and the water; (c) introducing the feed stream into the first fixed bed vessel, and contacting together, within said first fixed bed vessel, the brominated hydrocarbon and the ion exchange resin, thereby replacing at least one replaceable bromo group of the brominated hydrocarbon with a chloro group, and converting at least a portion of the brominated hydrocarbon to the chlorinated hydrocarbon; and (d) withdrawing a product stream from the first fixed bed vessel, wherein the product stream comprises the chlorinated hydrocarbon.

In further additional accordance with the present invention, there is also provided a method of forming a dried ion exchange resin comprising: (a) providing a fixed bed vessel comprising a fixed bed comprising a wet ion exchange resin, wherein the wet ion exchange resin comprises a first amount of water; (b) contacting together, within the fixed bed vessel, the wet ion exchange resin and a heated hydrocarbon vapor that forms an azeotrope with water of the wet ion exchange resin, thereby forming a wet vapor comprising hydrocarbon vapor and water vapor; and (c) removing the wet vapor from the fixed bed vessel, thereby forming the dried ion exchange resin comprising a second amount of water, wherein the second amount of water is less than the first amount of water.

The features that characterize the present invention are pointed out with particularity in the claims, which are annexed to and form a part of this disclosure. These and other features of the invention, its operating advantages and the specific objects obtained by its use will be more fully understood from the following detailed description in which non-limiting embodiments of the invention are illustrated and described.

DETAILED DESCRIPTION OF THE INVENTION

Figure 1:
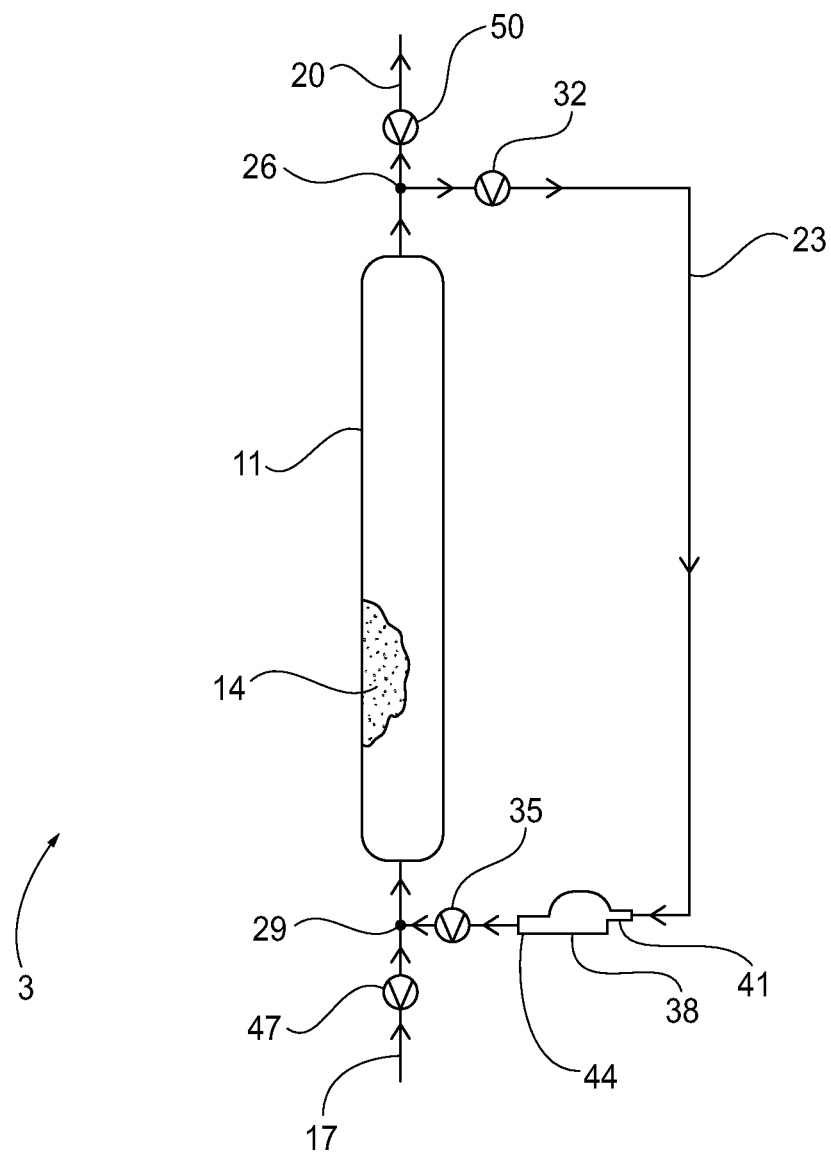
FIG. 1 is a schematic representation of a process assembly that includes a first fixed bed vessel, which can be used in the method of the present invention.

As used herein, spatial or directional terms, such as "left", "right", "inner", "outer", "above", "below", and the like, relate to the invention as it is shown in the drawing figures. However, it is to be understood that the invention can assume various alternative orientations and, accordingly, such terms are not to be considered as limiting.

Unless otherwise indicated, all numbers expressing quantities of ingredients, reaction conditions, processing parameters, physical characteristics, dimensions, and the like used in the specification and claims are to be under stood as modified in all instances by the term "about."

Unless otherwise indicated, all ranges or ratios disclosed herein are to be understood to encompass any and all subranges or subratios subsumed therein. For purposes of non-limiting illustration, a stated range or ratio of "1 to 10" should be considered to include any and all subranges between (and inclusive of) the minimum value of 1 and the maximum value of 10; that is, all subranges or subratios beginning with a minimum value of 1 or more and ending with a maximum value of 10 or less, such as but not limited to, 1 to 3.3, 4.7 to 7.5, 5.5 to 10, and the like.

As used herein, the articles "a," "an," and "the" include plural referents unless otherwise expressly and unequivocally limited to one referent.

As used herein, the term "aliphatic" and related terms, such as "aliphatic hydrocarbon(s)," "linear or branched aliphatic hydrocarbon(s)," "aliphatic hydrocarbon groups," and "linear or branched hydrocarbon groups" means non-cyclic and non-aromatic hydrocarbons, which: include at least one carbon atom, such as 1 to 20 carbon atoms, such as $C_1$-$C_{20}$ aliphatic hydrocarbons, or $C_1$-$C_{10}$ aliphatic hydrocarbons, or $C_1$-$C_6$ aliphatic hydrocarbons; can be linear or branched; optionally include one or more interior and/or terminal alkene (or alkenyl) groups; and optionally included one or more interior and/or terminal alkyne (or alkynyl) groups. When including two or more alkene groups, the alkene groups of an aliphatic group can be conjugated and/or non-conjugated. When including two or more alkyne groups, the alkyne groups of an aliphatic group can be conjugated and/or non-conjugated. When including at least one alkene group and at least one alkyne group, the alkene and alkyne groups of the aliphatic group can be conjugated and/or non-conjugated relative to each other.

Examples of aliphatic hydrocarbons include, but are not limited to, alkanes. As used herein, the term "alkane" and related terms, such as "alkane groups" means compounds or groups which: include at least one carbon atom, such as 1 to 20 carbon atoms, such as $C_1$-$C_{20}$ alkanes, or $C_1$-$C_{10}$ alkanes, or $C_1$-$C_6$ alkanes; are linear or branched; and are saturated (and correspondingly are free of alkene groups and alkyne groups). Examples of alkane groups include, but are not limited to, methane, ethane, n-propane, iso-propane, n-butane, iso-butane, sec-butane, t-butane, linear or branched pentane, linear or branched hexane, linear or branched heptane, linear or branched octane, linear or branched nonane, linear or branched decane, linear or branched undecane, linear or branched dodecane, linear or branched tridecane, linear or branched tetradecane, linear or branched pentadecane, linear or branched hexadecane, linear or branched heptadecane, linear or branched octadecane, linear or branched nonadecane, and linear or branched eicosane.

As used herein, recitations of "linear or branched," such as, but not limited to, linear or branched alkane, are herein understood to include, for purposes of non-limiting illustration: methane or a methyl group; compounds and groups that are linear, such as linear $C_2$-$C_{20}$ alkanes or linear $C_2$-$C_{20}$ alkyl groups; and groups that are appropriately branched, such as, but not limited to, branched $C_3$-$C_{20}$ alkanes or branched $C_3$-$C_{20}$ alkyl groups.

Examples of aliphatic groups include, but are not limited to, alkenes. As used herein, the term "alkene" and related terms, such as "alkene groups" means groups which: include at least two carbon atoms, such as 2 to 20 carbon atoms, such as $C_2$-$C_{20}$ alkenes, or $C_2$-$C_{10}$ alkenes, or $C_2$-$C_6$ alkenes; are linear or branched; and include one or more interior and/or terminal alkene (or alkenyl) groups. Examples of alkenes include, but are not limited to, those examples of linear or branched alkanes recited previously herein, which have at least two carbon atoms and at least one alkene (or alkenyl) group, such as, but not limited to, ethene, propene, linear or branched butene, linear or branched pentene, linear or branched hexene, etc.

Examples of aliphatic groups include, but are not limited to, alkynes. As used herein, the term "alkyne" and related terms, such as "alkyne group(s)" means groups which: include at least two carbon atoms, such as 2 to 20 carbon atoms, such as $C_2$-$C_{20}$ alkynes, or $C_2$-$C_{10}$ alkynes, or $C_2$-$C_6$ alkynes; are linear or branched; and include one or more interior and/or terminal alkyne (or alkynyl) groups. Examples of alkynes include, but are not limited to, those examples of linear or branched alkanes recited previously herein, which have at least two carbon atoms and at least one alkyne (or alkynyl) group, such as, but not limited to, ethyne, propyne, butyne, linear or branched pentyne, linear or branched hexyne, etc.

As used herein, the term "alicyclic" and related terms, such as "alicyclic hydrocarbon," "alicyclic hydrocarbon group," "cycloaliphatic," "cycloaliphatic hydrocarbon," and "cycloaliphatic hydrocarbon group" means cyclic and non-aromatic hydrocarbons, which: include at least three carbon atoms, such as 3 to 20 carbon atoms, such as $C_3$-$C_{20}$ alicyclic hydrocarbons, or $C_3$-$C_{10}$ alicyclic hydrocarbons, or $C_3$-$C_8$ alicyclic hydrocarbons; optionally include at least one unsaturated group selected from alkene and/or alkyne; and optionally include two or more fused alicyclic (or cycloaliphatic) rings.

Examples of alicyclic hydrocarbons and groups include, but are not limited to, cycloalkanes and cycloalkane groups. As used herein, the term "cycloalkane" and related terms, such as "cycloalkane group(s)" means groups which: include at least three carbon atoms, such as 3 to 20 carbon atoms, such as $C_3$-$C_{20}$ cycloalkanes, or $C_3$-$C_{10}$ cycloalkanes, or $C_3$-$C_8$ cycloalkanes; optionally include at least one unsaturated group selected from alkene and/or alkyne; and optionally include two or more fused cycloalkane rings. Examples of cycloalkanes include, but are not limited to: cyclopropane; cyclobutane; cyclopentane; cyclohexane; cycloheptane; cyclooctane; cyclononane; cyclodecane; cycloundecane; cyclododecane; bicyclo[2.2.1]heptane; decahydronaphthalene; tetradecahydroanthracene; tetradecahydrophenanthrene; and dodecahydro-1H-phenalene.

As used herein, the term "aromatic hydrocarbon" and related terms, such as "aromatic hydrocarbon group(s)" means cyclic aromatic hydrocarbon groups, which: include at least 5 carbon atoms, such as $C_5$-$C_{20}$ aromatic hydrocarbons, or $C_5$-$C_{14}$ aromatic hydrocarbons; and optionally include at least two fused aromatic hydrocarbon rings. Examples of aromatic hydrocarbons include, but are not limited to, benzene, naphthalene, anthracene, phenanthrene, and 1H-phenalene.

As used herein, the term "halogen" and related terms, such as "halogen group(s)" and/or "halo group(s)" means a single bonded halogen atom, such as selected from fluoro (F), chloro (Cl), bromo (Br), and/or iodo (I).

As used herein, and unless otherwise explicitly stated, the term "hydrogen" and related terms, such as "hydrogen group(s)" means a single bonded hydrogen (—H).

All documents, such as but not limited to issued patents and patent applications, referred to herein, and unless otherwise indicated, are to be considered to be "incorporated by reference" in their entirety.

The brominated hydrocarbons used in the method of the present invention, each include at least one replaceable bromo group (—Br). The term "replaceable bromo group" as used herein means a covalently bonded bromo group that can be replaced with a covalently bonded chloro group (—Cl). More particularly, each replaceable bromo group, of the brominated hydrocarbon, is covalently bonded to a $sp^3$ hybridized carbon. Correspondingly, replacement of a replaceable bromo group with a chloro group results in a chloro group that is covalently bonded to an $sp^3$ hybridized carbon, and more particularly a chloro group that is covalently bonded to the same $sp^3$ hybridized carbon to which was previously bonded the replaceable bromo group that has been so replaced.

For purposes of non-limiting illustration, the $sp^3$ hybridized carbon to which is bonded at least one bromo group is, with some embodiments, a pendent or terminal group, such as represented by the following Formula (A),

(A)

With reference to Formula (A), subscript x is 1 to 3, and each Y (that is present) is independently hydrogen, chlorine, a hydrocarbon group, or a halogenated hydrocarbon group where each halogen is independently selected from chloro and bromo. The brominated hydrocarbon, with some embodiments, includes at least one $sp^3$ hybridized carbon (to which is bonded at least one bromo group) represented by Formula (A).

With some further embodiments, and for purposes of further non-limiting illustration, the $sp^3$ hybridized carbon to which is bonded at least one bromo group is part of an alicyclic hydrocarbon ring, such as represented by the following Formula (B):

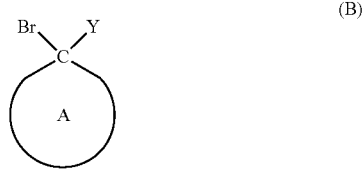

(B)

With reference to Formula (B), Ring A is an alicyclic hydrocarbon, such as described previously herein, and Y is hydrogen, chlorine, bromine, a hydrocarbon group, or a halogenated hydrocarbon group where each halogen is independently selected from chloro and bromo. Ring A of Formula (B) optionally includes, with some embodiments: (i) at least one further $sp^3$ hybridized ring carbon, each of which independently has bonded thereto at least one bromo group, such as depicted in Formula (B); and/or (ii) at least one pendent $sp^3$ hybridized carbon having at least one bromo group bonded thereto, such as represented by Formula (A).

With some embodiments, the brominated hydrocarbon and chlorinated hydrocarbon product are each liquid at ambient conditions, such as a temperature of 22° C. and a pressure of 1 atmosphere.

The brominated hydrocarbon, with some embodiments, is selected from brominated linear or branched aliphatic hydrocarbons, brominated alicyclic hydrocarbons, aromatic hydrocarbons that include at least one brominated linear or branched aliphatic hydrocarbon group and/or at least one brominated alicyclic hydrocarbon group, and combinations thereof.

The brominated hydrocarbon, with some further embodiments, is selected from brominated linear or branched $C_1$-$C_{20}$ alkanes, brominated $C_3$-$C_8$ cycloalkanes, benzene having at least one brominated linear or branched $C_1$-$C_{20}$ alkyl group, and combinations thereof.

The brominated hydrocarbon, with some embodiments, further includes at least one $sp^3$ hybridized carbon having at least one chloro group covalently bonded thereto, in which the $sp^3$ hybridized carbon having at least one chloro group bonded thereto is the same or different than the $sp^3$ hybridized carbon having at least one replaceable bromo group bonded thereto.

With some embodiments, the brominated hydrocarbon includes 1-bromo-2-chloroethane, and the chlorinated hydrocarbon includes 1,2-dichloroethane.

The ion exchange resin including chloride groups ($Cl^-$ groups), used with some embodiments of the method of the present invention, includes an organic polymer, (such as, but not limited to, polystyrene and styrene-divinylbenzene copolymer) to which is bonded a plurality of groups, which are each independently composed of: (i) a cation portion, such as a quaternary ammonium group; and (ii) an anion portion including one or more chloride ($Cl^-$) groups. The ion exchange resin including chloride groups is, with some further embodiments, in the form of beads having any suitable particle size, such as beads having a diameter of from 0.5 mm to 10 mm, or from 0.5 mm to 5 mm, or from 0.5 mm to 1.0 mm. The organic polymer of the ion exchange resin including chloride groups is, with some embodiments, crosslinked. The ion exchange resin including chloride groups, used with some embodiments of the method of the present invention, is selected from art-recognized ion exchange resins, and can be referred to as an anion exchange resin including chloride groups. The ion exchange resin including chloride groups is also and equivalently referred to herein as a/the chlorinated ion exchange resin.

With some embodiments the ion exchange resin is selected from: gel-type ion exchange resins (e.g., having an average pore size of from 0.1 nm to 100 nm, or from 0.1 nm to 50 nm, or from 0.1 nm to 20 nm, or from 1 nm to 2 nm); macroporous-type ion exchange resins (e.g., having an average pore size of from 5 nm to 20,000 nm, or from 10 nm to 10,000 nm, or from 15 nm to 5000 nm, or from 20 nm to 100 nm); or combinations thereof. In accordance with some embodiments, the ion exchange resin of the present methods is selected from macroporous-type ion exchange resins. In accordance with some embodiments of the present invention, macroporous-type ion exchange resins provide improved reaction kinetics, as compared to gel-type ion exchange resins.

The ion exchange resin, when contacted with the brominated hydrocarbon, includes water (or has a water content) of less than or equal to 30 percent by weight, or less than or equal to 25 percent by weight, or less than or equal to 20 percent by weight, or less than or equal to 15 percent by weight, or less than or equal to 10 percent by weight, or less than or equal to 5 percent by weight, the percent weights in each case being based on the total weight of the ion exchange resin and the water. The ion exchange resin, when contacted with the brominated hydrocarbon, includes water (or has a water content) of greater than or equal to 0 percent by weight, or greater than or equal to 1 percent by weight or greater than or equal to 2 percent by weight, the percent weights in each case being based on the total weight of the ion exchange resin and the water. The water content of the ion exchange resin, when contact with the brominated hydrocarbon, with some embodiments, includes an amount of water that ranges between any combination of the previously recited lower and upper amounts, such as, but not limited to, from 0 percent by weight to 30 percent by weight, or from 0 percent by weight to 25 percent by weight, or from 0 percent by weight to 20 percent by weight, or from 0 percent by weight to 15 percent by weight, or from 0 percent by weight to 10 percent by weight, or from 1 percent by weight to 10 percent by weight, or from 2 percent by weight to 10 percent by weight, or from 0 percent by weight to 5 percent by weight, or from 1 percent by weight to 5 percent by weight, or from 2 percent by weight to 5 percent by weight, the percent weights in each case being based on the total weight of the ion exchange resin and the water.

With some embodiments, the ion exchange resin, when contacted with the brominated hydrocarbon, includes water (or has a water content) of from 0.5 percent by weight to 30 percent by weight, or of from 1 percent by weight to 30 percent by weight, or from 1 percent by weight to 20 percent by weight, or 1 percent by weight to 15 percent by weight, or from 1 percent by weight to 10 percent by weight, or from 2 percent by weight to 10 percent by weight, or from 1 percent by weight to 5 percent by weight, or from 2 percent by weight to 5 percent by weight, or from 1 percent by weight to 4 percent by weight, or from 2 percent by weight to 4 percent by weight, the percent weights in each case being based on the total weight of the ion exchange resin and the water.

The water content of the ion exchange resin is determined, with some embodiments, by obtaining an initial weight of the ion exchange resin, exposing the ion exchange resin to elevated temperature for a period of time (such as 105° C. for 20 hours), obtaining a final weight of the ion exchange resin after exposure to the elevated temperature, and comparing the initial and final weight values. With some further embodiments, the water content of the ion exchange resin is determined by volumetric Karl Fischer titration and/or coulometric Karl Fischer titration.

With some embodiments, the ion exchange resin has a molar equivalents of chloride groups, the brominated hydrocarbon has a molar equivalents of replaceable bromo groups, and a ratio of the molar equivalents of chloride groups of the ion exchange resin to the molar equivalents of replaceable bromo groups of the brominated hydrocarbon is at least 0.5:1, or at least 1:1.

The ratio of the molar equivalents of chloride groups of the ion exchange resin to the molar equivalents of replaceable bromo groups of the brominated hydrocarbon is, with some embodiments, from 0.5:1 to 100:1, or from 0.5:1 to 10:1, or from 0.5:1 to 4:1, or from 1:1 to 4:1.

In accordance with some embodiments of the method of the present invention, the recitation of "at least a portion of the brominated hydrocarbon is converted to the chlorinated hydrocarbon," means at least some percent by moles of brominated hydrocarbon is converted to the chlorinated hydrocarbon, based on initial moles of brominated hydrocarbon. With some embodiments, at least 10 percent by moles of the brominated hydrocarbon, or at least 25 percent by moles of the brominated hydrocarbon, or at least 30 percent by moles of the brominated hydrocarbon or at least 50 percent by moles of the brominated hydrocarbon, or at least 75 percent by moles of the brominated hydrocarbon, or at least 80 percent by moles of the brominated hydrocarbon, or at least 90 percent by moles of the brominated hydrocarbon, or at least 95 percent by moles of the brominated hydrocarbon, or 100 percent by moles of the brominated hydrocarbon, is in each case converted to the chlorinated hydrocarbon, the percent by moles in each case being based on initial moles of brominated hydrocarbon.

Contacting the brominated hydrocarbon with the ion exchange resin can be conducted over a wide range of temperatures, such as greater than 0° C. and less than or equal to 400° C., with some embodiments. With some embodiments, each of the brominated hydrocarbon and optional organic solvent are in liquid form when contacted together with the ion exchange resin. The operating conditions, such as temperature and/or pressure, can be adjusted with some embodiments to maintain each of the brominated hydrocarbon, optional organic solvent, and the chlorinated hydrocarbon product in liquid form during the method of the present invention.

Contacting together the brominated hydrocarbon and the ion exchange resin is conducted, with some embodiments, at a temperature that is greater than room temperature, such as an elevated temperature that is greater than 22° C., or greater than 25° C., or greater than or equal to 30° C., or greater than or equal to 40° C., or greater than or equal to 50° C. With some further embodiments, contacting together the brominated hydrocarbon and the ion exchange resin is conducted at a temperature of at least 30° C. (or at least 50° C.), and a molar conversion (or percent molar conversion) of the brominated hydrocarbon to the chlorinated hydrocarbon is at least 30 percent, based on initial moles of brominated hydrocarbon. With some further embodiments, the molar conversion (or percent molar conversion) of the brominated hydrocarbon to the chlorinated hydrocarbon is at least 30 percent, or at least 90 percent, or at least 95 percent, or at least 98 percent, and less than or equal to 100 percent, where each percent is based on initial moles of the brominated hydrocarbon.

Contacting together the brominated hydrocarbon and the ion exchange resin is conducted, with some embodiments, at a temperature of from 30° C. to 200° C., or from 50° C. to 177° C., or from 60° C. to 125° C., or from 70° C. to 110° C., or from 80° C. to 100° C., or from 85° C. to 95° C., inclusive of the recited temperature values.

In accordance with some embodiments of the present invention, when the brominated hydrocarbon and the ion exchange resin are contacted together, the ion exchange resin includes water (or has a water content) of from 1 percent by weight to 10 percent by weight, or from 2 percent by weight to 10 percent by weight, or from 1 percent by weight to 5 percent by weight, or from 2 percent by weight to 5 percent by weight, inclusive of the recited values, and where the percent weights in each case are based on the total weight of the ion exchange resin and the water.

Contacting together the brominated hydrocarbon and the ion exchange resin is conducted, with some embodiments, in the presence of an organic solvent, where the organic solvent is selected from hydrocarbons, chlorinated hydrocarbons that are free of bromo groups, and combinations thereof. The organic solvent, with some embodiments, is or includes the product chlorinated hydrocarbon that results from conversion of the brominated hydrocarbon. With some embodiments, the organic solvent is selected from one or more chloroalkanes, chloroalkenes, and chloroalkynes. With some further embodiments, the organic solvent is selected from one or more linear or branched $C_1$-$C_{20}$ chloro-alkanes that includes at least one chloro group (and in which less than all hydrogens thereof is replaced with a chloro group). With some further embodiments, the organic solvent is selected from: chloromethanes, such as methylene dichloride (or dichloromethane), trichloromethane, and carbon tetrachloride; chloroethanes, such as dichloroethanes and trichloroethanes; chloroethylenes, such as tetrachloroethylene; chloropropanes, such as trichloropropanes and pentachloropropanes; and combinations thereof. The organic solvent, with some embodiments, is selected from 1,1-dichloroethane, 1,2-dichloroethane, 1,1,2-trichloroethane, tetrachloroethylene, and combinations thereof.

The method of the present invention can be conducted under batch conditions, continuous conditions, or a combination thereof. With some embodiments, the method of the present invention is conducted under batch conditions, which involves contacting together the brominated hydrocarbon, the chlorinated ion exchange resin, and optionally an organic solvent in a suitable vessel, such as a reactor, to form a heterogeneous mixture. The heterogeneous mixture, with some embodiments, is subjected to agitation or stirring, such as by an impeller, and an optional increase in temperature for a period of time, during which and/or after-which samples are taken to determine the degree (or extent) of conversion of the brominated hydrocarbon to the product chlorinated hydrocarbon. After a desired degree (or extent) of conversion has been achieved, the ion exchange resin is separated from the liquid portion of the heterogeneous mixture, such as by filtering. The isolated liquid portion, with some embodiments, is optionally subjected to art-recognized work-up procedures for purposes of further isolating and/or purifying the product chlorinated hydrocarbon.

The method of the present invention is, with some further embodiments, conducted under continuous conditions, which involves introducing continuously a feed stream that includes the brominated hydrocarbon, into a fixed bed vessel that includes the chlorinated ion exchange resin, and removing continuously, from the fixed bed vessel, a product stream that includes the product chlorinated hydrocarbon. With some further embodiments, at least a portion of the product stream (that includes the product chlorinated hydrocarbon) is re-introduced continuously into the fixed bed vessel that includes the chlorinated ion exchange resin. When, with some embodiments, a desired level of conversion of the brominated hydrocarbon to product chlorinated hydrocarbon is reached, the feed stream and optional recycle stream are stopped, the product chlorinated hydrocarbon is isolated, and the ion exchange resin is regenerated.

For purposes of non-limiting illustration, and in accordance with some embodiments, a method of converting a brominated hydrocarbon to a chlorinated hydrocarbon is described with reference to FIG. 1. With reference to FIG. 1, there is schematically depicted a process assembly 3 that includes a first fixed bed vessel 11 that includes therein a first fixed bed 14 that includes an ion exchange resin including chloride ($Cl^-$) groups. First fixed bed vessel 11 is depicted with a partial cut-away thereof for purposes of illustrating the first fixed bed 14. With some embodiments, the first fixed bed 14 is defined by the chlorinated ion exchange resin. The first fixed bed vessel can be fabricated from any suitable material or combination of materials including, for example, metal (such as stainless steel), glass, plastics (including thermoplastics and/or crosslinked plastics), fiberglass filled plastics, and combinations thereof.

With some embodiments, the chlorinated ion exchange resin of the first fixed bed 14, as initially loaded into first fixed bed vessel 11, includes water in an amount of less than or equal to 70 percent by weight, or less than or equal to 50 percent by weight, less than or equal to 30 percent by weight, or less than or equal to 25 percent by weight, or less than or equal to 20 percent by weight, or less than or equal to 15 percent by weight, or less than or equal to 10 percent by weight, or less than or equal to 5 percent by weight, or less than or equal to 4 percent by weight, or less than or equal to 3 percent by weight, the percent weights in each case being based on total weight of the chlorinated ion exchange resin.

Figure 2:
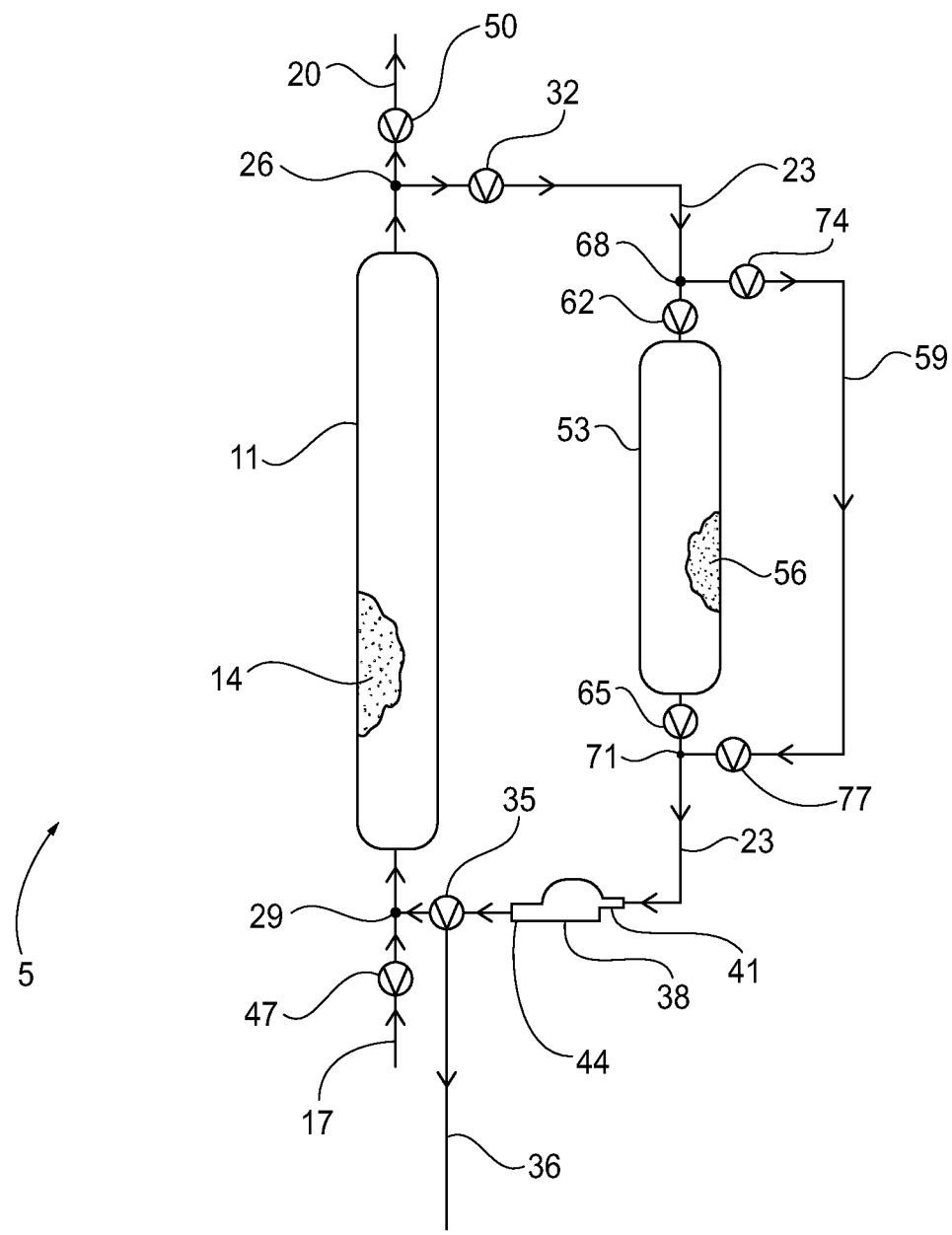
FIG. 2 is a schematic representation of a process assembly that includes a first fixed bed vessel and a second fixed bed vessel, which can be used in the method of the present invention.

In accordance with some embodiments of the method of the present invention, there is provided a feed stream that includes the brominated hydrocarbon (which includes at least one replaceable bromo group, in which each replaceable bromo group is independently covalently bonded to a $sp^3$ hybridized carbon, as described previously herein). With further reference to FIG. 1, the feed stream is passed through conduit 17 and introduced into the first fixed bed vessel 11. Within the first fixed bed vessel 11, the brominated hydrocarbon of the first feed stream and the chlorinated ion exchange resin of the first fixed bed 14 are contacted together, which results in conversion of at least a portion of the brominated hydrocarbon to the chlorinated hydrocarbon (or product chlorinated hydrocarbon). In FIG. 1 and FIG. 2, the flow direction of the various streams through the conduits is indicated by arrows.

With further reference to FIG. 1, a product stream that includes the product chlorinated hydrocarbon is withdrawn from the first fixed bed vessel 11 through outlet conduit 20, and with some embodiments, forwarded downstream to a storage vessel (not shown) and/or for further processing, such as work-up procedures.

With some embodiments, at least a portion of the product stream, which includes the product chlorinated hydrocarbon, is introduced back into the first fixed bed vessel. With reference to FIG. 1 and in accordance with some embodiments, at least a portion of the product stream is re-introduced into the first fixed bed vessel 11 through a recycle conduit 23 (or recycle circuit 23). The recycle conduit 23 has a first T-intersection 26 with outlet conduit 20, and a second T-intersection 29 with inlet conduit 17. The recycle conduit, with some embodiments, includes: a first recycle valve 32 that is positioned down-stream from the first T-intersection 26; a second recycle valve 35 that is positioned up-stream from second T-intersection 29; and optionally a pump 38 that is positioned inline between first recycle valve 32 and second recycle valve 35 (down-stream from first recycle valve 32 and up-stream from second recycle valve 35). Pump 38 includes an inlet 41 and an outlet 44.

In accordance with some embodiments, and with further reference to FIG. 1, inlet conduit 17 includes an inlet valve 47 that is positioned up-stream from second T-intersection 29, and outlet conduit 20 includes an outlet valve 50 that is positioned down-stream from first T-intersection 26. The process assembly 3 depicted in FIG. 1 can, with some embodiments, include more valves or fewer valves placed in alternate positions, such as at the first T-intersection 26 and/or at the second T-intersection 29.

In accordance with some embodiments and with further reference to FIG. 1, after introducing continuously the feed stream through inlet conduit 17 and into first fixed bed 11, and withdrawing continuously the product stream from the first fixed bed 11 through outlet conduit 20, inlet valve 47 and outlet valve 50 are each at least partially closed, first recycle valve 32 and second recycle valve 35 are at least partially opened, and pump 38 is activated. The sequence of valve closings, valve openings, and pump activation can be modified accordingly, and/or conducted manually and/or remotely, such as by one or more electrical connections (not shown). With outlet valve 50 at least partially closed, at least a portion of the product stream passes through first T-intersection 26, through first recycle valve 32, and through/into recycle conduit 23, into pump inlet 41, through pump 38, through pump outlet 44, through second recycle valve 35, through second T-intersection 29, through inlet conduit 17 and into first fixed bed 11. Recycling the product stream through the first fixed bed 11 is conducted, with some embodiments, for a period of time during which one or more samples are withdrawn and analyzed to determine whether a desired extent of conversion of brominated hydrocarbon to chlorinated hydrocarbon has been achieved. When a desired extent of conversion of brominated hydrocarbon to chlorinated hydrocarbon has been achieved, the various valves can be adjusted so as to allow the product stream to be removed from the first fixed bed 11 through outlet conduit 20 and forwarded downstream for further processing and/or storage.

The method of the present invention further includes, with some embodiments: providing a second fixed bed vessel including a second fixed bed that includes a drying agent; introducing at least a portion of the product stream into the second fixed bed vessel where it contacts the drying agent, thereby removing at least a portion of residual water from the product stream, and forming a dried product stream; and removing the dried product stream from the second fixed bed vessel. With some embodiments, the drying agent in the second fixed bed vessel is selected from $CaCl_2$, alumina, silica, molecular sieves, and combinations of two or more thereof.

With some embodiments, the product stream includes residual water in an amount of less than or equal to 1 percent by weight, or less than or equal to 0.5 percent by weight, or less than or equal to 0.25 percent by weight, or less than or equal to 0.1 percent by weight, the percent weights in each case being based on the total weight of the product stream.

With reference to FIG. 2, there is schematically depicted a process assembly 5, which includes portions of process assembly 3 of FIG. 1, and further includes a second fixed bed vessel 53 that includes a second fixed bed 56 including a drying agent (such as being composed of $CaCl_2$ with some embodiments). The $CaCl_2$ is, with some embodiments, present in particulate form. The particulate $CaCl_2$ can have any suitable particle sized, such as an average particle sized of from 1 mm to 50 mm, or from 6 mm to 13 mm. Second fixed bed vessel 53 is depicted with a partial cut-away thereof for purposes of illustrating the second fixed bed 56. With some embodiments, the second fixed bed 56 is defined by the drying agent, such as $CaCl_2$. The second fixed bed vessel 53 is positioned inline in recycle conduit 23, with some embodiments.

The process assembly 5, with some embodiments, includes a bypass conduit 59 that bypasses the second fixed bed vessel 53. The second fixed bed vessel 53 includes a second fixed bed vessel inlet valve 62 and a second fixed bed vessel outlet valve 65. Bypass conduit 59 has a first bypass T-intersection 68 with recycle conduit 23, and a second bypass T-intersection 71 with recycle conduit 23. The first bypass T-intersection 68 is positioned up-stream from the second fixed bed inlet valve 62, and the second bypass T-intersection 71 is positioned down-stream from the second fixed bed vessel outlet valve 65. Bypass conduit 59 includes a first bypass valve 74 and a second bypass valve 77. First bypass valve 74 is positioned down-stream from first bypass T-intersection 68, and second bypass valve 77 is positioned up-stream from second bypass T-intersection 71.

With reference to FIG. 2, and in accordance with some embodiments, with the feed stream introduced continuously through inlet conduit 17 and into/through first fixed bed 11: inlet valve 47 and outlet valve 50 of the first fixed bed 11 are each at least partially closed; first recycle valve 32 and second recycle valve 35 are each at least partially opened; second fixed bed inlet valve 62 and second fixed bed outlet valve 65 are each at least partially opened; and first bypass valve 74 and second bypass valve 77 are each closed. With the valves of process assembly 5 of FIG. 2 so arranged, at least a portion of the product stream passes through recycle conduit 23 and into second fixed bed vessel 53 wherein it contacts second fixed bed 56 including $CaCl_2$, which results in the formation of a dried product stream that is removed from second fixed bed 56 through second fixed bed vessel outlet valve 65.

The dried product stream removed from the second fixed bed vessel 53 can be forwarded downstream for storage and/or further processing through one or more further conduits, such as through conduit 36, with valve 35 appropriately turned (or adjusted). With some embodiments, the method of the present invention further includes introducing at least a portion of the dried product stream into the first fixed bed vessel. With reference to FIG. 2, and in accordance with some embodiments, the dried product stream is forwarded through pump 38, through second recycle valve 35, through second T-intersection 29, through inlet conduit 17 and into first fixed bed vessel 11. The dried product stream can be passed numerous times through the first fixed bed 11 and the second fixed bed 53 for purposes of further drying the product stream. With the various valves adjusted accordingly (such as described previously herein), the dried product stream is passed through outlet conduit 20 and forwarded downstream for further processing and/or storage.

With reference to FIG. 2, the second fixed bed vessel 53 can be bypassed, with some embodiments, by: closing the second fixed bed vessel inlet valve 62 and closing the second fixed bed outlet valve 65; and opening the first bypass valve 74 and opening the second bypass valve 77. With the valves so arranged, the recycle conduit and the bypass conduit 59 together serve as a combined recycle conduit 23-59 that bypasses the second fixed bed vessel 53.

With some further embodiments, the chlorinated ion exchange resin of the first fixed bed, as initially loaded into first fixed bed vessel 11, includes water in an amount of greater than 30 percent by weight, such as greater than or equal to 50 percent by weight, or greater than or equal to 70 percent by weight, and can be referred to as a water-wet chlorinated ion exchange resin (or wet chlorinated ion exchange resin, or wet ion exchange resin). Prior to introduction of the feed stream including brominated hydrocarbon into the first fixed bed vessel 11, the water-wet chlorinated ion exchange resin is subjected to one or more dewatering or drying processes, with some embodiments. Examples of such dewatering or drying processes include, but are not limited to, subjecting the wet ion exchange resin to an azeotropic drying process, and/or contacting together the wet ion exchange resin and a drying gas, such as optionally heated nitrogen gas, which are each described in further detail herein.

With some embodiments, the ion change resin of the first fixed bed has a molar equivalents of chloride groups, the first fixed bed vessel including the first fixed bed has a maximum static feed volume, a volume of the feed stream that is equivalent to the maximum static feed volume provides a maximum static molar equivalents of replaceable bromo groups, and a ratio of the molar equivalents of chloride groups of the ion exchange resin to the maximum static molar equivalents of replaceable bromo groups is at least 0.5:1, or at least 1:1.

As used herein, the term "maximum static feed volume" of the first fixed bed vessel including the first fixed bed, means the maximum volume of feed (or feed stream) that can be accommodated by the first fixed bed vessel including the first fixed bed, in a single pass, or if operated under static or batch conditions (rather than continuous conditions), and is also referred to as "a column volume" or "a void volume" of the first fixed bed vessel including the first fixed bed. Correspondingly, a volume of the feed stream that is equivalent to the maximum static feed volume (of the first fixed bed) provides a maximum static molar equivalents of replaceable bromo groups. Further, and in accordance with some embodiments of the present invention, a ratio of the molar equivalents of chloride groups of the ion exchange resin to the maximum static molar equivalents of replaceable bromo groups is at least 0.5:1 (or at least 1:1), at least for the first maximum static feed volume (of the feed stream) that is passed through the first fixed bed vessel.

In accordance with some further embodiments of the present invention, the ratio of the molar equivalents of chloride groups of the ion exchange resin (of the first fixed bed of the first fixed bed vessel) to the maximum static molar equivalents of replaceable bromo groups is from 0.5:1 to 100:1, or from 0.5:1 to 10:1, or from 0.5:1 to 4:1, or from 1:1 to 4:1.

Contacting together the brominated hydrocarbon and the ion exchange resin (within the first fixed bed vessel), is conducted at a temperature that is greater than room temperature, such as an elevated temperature that is greater than 22° C., or greater than 25° C., or greater than or equal to 30° C., or greater than or equal to 40° C., or greater than or equal to 50° C. In accordance with some embodiments of the present invention, contacting together the brominated hydrocarbon and the ion exchange resin (within the first fixed bed vessel), is conducted at a temperature of at least 30° C. (or at least 50° C.), and a molar conversion of the brominated hydrocarbon to the chlorinated hydrocarbon is at least 10 percent, or at least 25 percent, or at least 30 percent, or at least 50 percent, or at least 75 percent, or at least 80 percent, or at least 90 percent, based on total moles of brominated hydrocarbon passed through the first fixed bed vessel.

With some further embodiments involving the feed stream being passed through the first fixed bed vessel, the molar conversion (or percent molar conversion) of the brominated hydrocarbon to the chlorinated hydrocarbon is at least 30 percent, or at least 90 percent, or at least 95 percent, or at least 98 percent, and less than or equal to 100 percent, where each percent is based on total moles of brominated hydrocarbon passed through the first fixed bed vessel.

Contacting together the brominated hydrocarbon and the ion exchange resin (of the first fixed bed within the first fixed bed vessel) is conducted, with some embodiments, at a temperature of from 30° C. to 200° C., or from 50° C. to 177° C., or from 60° C. to 125° C., or from 70° C. to 110° C., or from 80° C. to 100° C., or from 85° C. to 95° C., inclusive of the recited temperature values. The temperature at which the brominated hydrocarbon and the ion exchange resin are contacted within the first fixed bed vessel is, with some embodiments, controlled by a heat exchange jacket (not shown) that envelopes at least a portion of the exterior of the first fixed bed vessel 11, and/or by passing the feed stream through a heat exchanger (not shown). With some embodiments, recycle conduit 23 includes a heat exchanger (not shown) that maintains the temperature of the recycled feed/product stream within a desired (or preselected) range.

In accordance with some embodiments of the method of the present invention, the first fixed bed (residing within the first fixed bed vessel) includes a wet ion exchange resin that includes water in an amount of greater than 30 percent by weight, based on the total weight of the ion exchange resin and the water. The method of the present invention further includes, with some embodiments, converting the wet ion exchange resin to the ion exchange resin comprising water in an amount of less than or equal to 30 percent by weight, based on the total weight of the ion exchange resin and the water. The conversion includes, with some embodiments, subjecting the wet ion exchange resin to an azeotropic drying process. The azeotropic drying process includes, with some embodiments, contacting together, within the first fixed bed vessel, the wet ion exchange resin and a heated hydrocarbon vapor that forms an azeotrope with water of the wet ion exchange resin, thereby forming a wet vapor that includes hydrocarbon vapor and water vapor. The method further comprises, with some embodiments, removing the wet vapor from the first fixed bed vessel, thereby forming the ion exchange resin including water in an amount of less than or equal to 30 percent by weight, based on the total weight of the ion exchange resin and the water.

With some embodiments, the azeotropic drying process is conducted prior to introducing the feed stream into the first fixed bed vessel.

The hydrocarbon of the heated hydrocarbon vapor is, with some embodiments, selected from non-halogen substituted hydrocarbon, halogen substituted hydrocarbon, or combinations thereof.

With some embodiments, the wet (or water-wet) ion exchange resin (or chlorinated ion exchange resin) includes water in an amount of greater than 30 percent by weight, such as greater than or equal to 35 percent by weight, or greater than or equal to 40 percent by weight, or greater than or equal to 45 percent by weight, or greater than or equal to 50 percent by weight, or greater than or equal to 70 percent by weight, in each case based on the total weight of the ion exchange resin and the water. With some further embodiments, the wet (or water-wet) ion exchange resin (or chlorinated ion exchange resin) includes water in an amount of from greater than 30 percent by weight to less than or equal to 200 percent by weight, or from greater than 30 percent by weight to less than or equal to 100 percent by weight, or from greater than 30 percent by weight to less than or equal to 90 percent by weight, or from greater than or equal to 50 percent by weight to less than or equal to 85 percent by weight, or from greater than or equal to 70 percent by weight to less than or equal to 80 percent by weight, the percent weights in each case based on the total weight of the ion exchange resin and the water.

The non-halogen substituted hydrocarbon of the heated hydrocarbon vapor, with some embodiments, is selected from one or more of those classes and examples of hydrocarbons recited previously herein, provided the hydrocarbon vapor thereof is capable of forming an azeotrope with water of the wet ion exchange resin. With some embodiments, classes and examples of the non-halogen substituted hydrocarbon of the heated hydrocarbon vapor include, but are not limited to: linear or branched alkanes, such as linear or branched $C_1$-$C_{20}$ alkanes; linear or branched alkenes, such as linear or branched $C_2$-$C_{20}$ alkenes; alicyclic hydrocarbons, such as $C_6$-$C_{20}$ cycloalkanes; and aromatic hydrocarbons, such as $C_5$-$C_{20}$ aromatic hydrocarbons, such as benzene, toluene, ethylbenzene, and xylenes. The halogen substituted hydrocarbon of the heated hydrocarbon vapor can, with some embodiments, be selected from halogenated versions of the hydrocarbons from which the non-halogenated hydrocarbon can be selected. The halogen substituted hydrocarbon, which some embodiments includes at least one halogen (such as Cl and/or Br). With some further embodiments, the halogen substituted hydrocarbon is a perhalogenated hydrocarbon, with each halogen thereof independently selected from Cl or Br, such as, but not limited to, tetrachloroethylene. With some embodiments, the hydrocarbon of the heated hydrocarbon vapor is a halogen substituted hydrocarbon selected from 1,2-dichloroethane, 1-bromo-2-chloroethane, trichloromethane (or chloroform), or combinations thereof.

As used herein, the term "vapor" with regard to the term "heated hydrocarbon vapor" means the heated hydrocarbon is in a gaseous phase. The temperature of the heated hydrocarbon vapor is selected such that it is capable of forming an azeotrope with the water of the wet ion exchange resin under the pressure within the first fixed bed vessel. With some embodiments, the pressure within the first fixed bed vessel during the azeotropic drying process is substantially ambient pressure, such as 1 atmosphere. With some embodiments, the temperature of the heated hydrocarbon vapor, when introduced into the first fixed bed vessel, is from 40° C. to 150° C., or from 60° C. to 150° C., or from 80° C. to 150° C., or from 84° C. to 110° C.

With some embodiments of the present invention, the heated hydrocarbon vapor is formed by passing liquid hydrocarbon through a heater or heat exchanger. With some further embodiments, the hydrocarbon vapor is formed by introducing liquid hydrocarbon into the fixed bed vessel containing the ion exchange resin, followed by heating the fixed bed vessel (such as, with a steam jacket), so as to convert the liquid hydrocarbon introduced therein to hydrocarbon vapor.

As used herein, the term "vapor" with regard to the term "water vapor" means water that is in a gaseous phase.

The azeotropic drying process is conducted prior to introducing the feed stream into the first fixed bed vessel. With some embodiments, the azeotropic drying process is conducted: (i) after the first fixed bed vessel has been loaded with wet ion exchange resin having a water content of greater than 30 percent by weight, based on the total weight of the ion exchange resin and the water; and (ii) prior to introducing the feed stream into the first fixed bed vessel. With some further embodiments, the azeotropic drying process is conducted: (i) after the first fixed bed vessel has been loaded with fresh ion exchange resin, and washing the fresh ion exchange resin with aqueous HCl containing, for example 4 percent by weight of HCl, which results in the formation of wet ion exchange resin having a water content of greater than 30 percent by weight, based on total weight of the ion exchange resin; and (ii) prior to introducing the feed stream into the first fixed bed vessel. With some additional embodiments, the azeotropic drying process is conducted: (i) after subjecting the ion exchange resin to regeneration by contact/washing with aqueous HCl containing, for example 4 percent by weight of HCl, which results in the formation of wet ion exchange resin having a water content of greater than 30 percent by weight, based on total weight of the ion exchange resin; and (ii) prior to introducing (or re-introducing) the feed stream into the first fixed bed vessel.

The wet vapor removed from the first fixed bed vessel, with some embodiments, includes hydrocarbon vapor and water vapor. The wet vapor removed from the first fixed bed vessel during the azeotropic drying process can, with some embodiments, be forwarded for further processing. With some embodiments, the wet vapor removed from the first fixed bed vessel during (or as a result of) the azeotropic drying process is introduced into a condenser, which converts the wet vapor into a wet liquid (or wet condensate) that includes liquid water and liquid hydrocarbon. The wet condensate is forwarded, with some embodiments, into phase a separator, which separates the wet condensate into an aqueous stream that includes water, and an organic stream that includes the hydrocarbon of the previously heated hydrocarbon vapor. The aqueous stream and the organic stream removed from the phase separator are each, with some embodiments, a liquid stream. The aqueous stream and/or the organic stream removed from the phase separator are, with some further embodiments, each forwarded for further processing, such as, but not limited to, one or more further separation/isolation processes.

Figure 3:
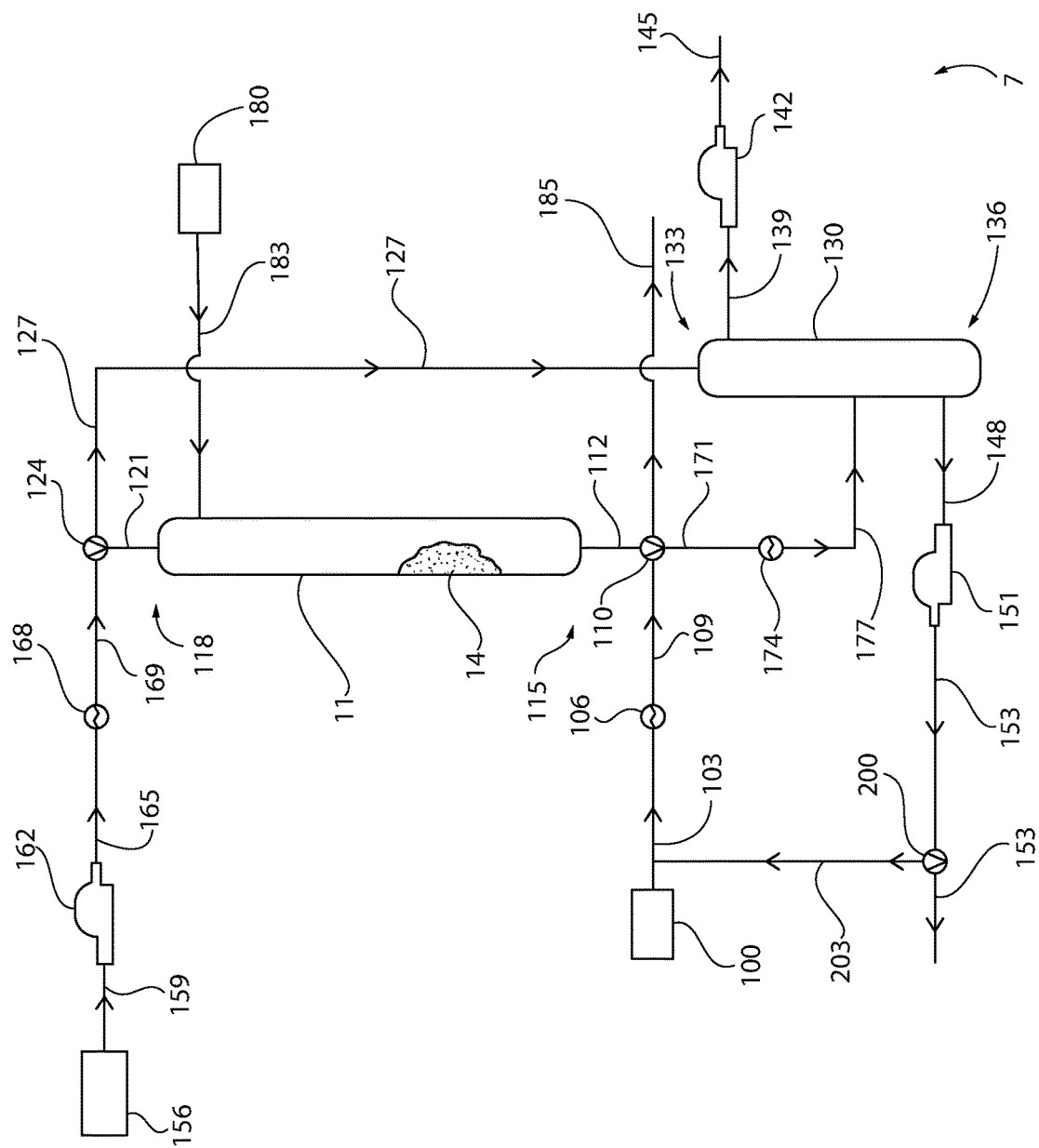
FIG. 3 is a schematic representation of a process assembly that can be used in the method of the present invention, which is adapted for azeotropic drying and acid washing/regeneration of the ion exchange resin, and in addition to a first fixed bed vessel, further includes a phase separator.

In accordance with some embodiments, the method of the present invention can be conducted using process assembly 7 as schematically depicted in FIG. 3. Process assembly 7 of FIG. 3 includes, in summary: first fixed bed vessel 11, which includes first fixed bed 14, which includes or is defined by the chlorinated ion exchange resin; phase separator 130; a source of feed represented by container 100; a source of hydrocarbon represented by container 156, for azeotropic drying of the ion exchange resin; and a source of aqueous HCl represented by container 180, for acid washing and/or regeneration of the ion exchange resin.

With some embodiments of the present invention, and with further reference to FIG. 3, a feed stream that includes brominated hydrocarbon and optionally an organic solvent is forwarded from container 100 through conduit 103, through preheater 106 (which heats the feed stream to, for example, 30° C. to 200° C. or 50° C. to 177° C.). From preheater 106, the heated feed is forwarded through conduit 109, through valve 110, which is positioned (or turned) so as to direct the heated feed stream up through conduit 112 and into lower portion 115 of first fixed bed vessel 11. The heated feed stream, as it passes up through the interior of first fixed bed vessel 11, contacts the chlorinated ion exchange resin of first fixed bed 14, which results in conversion of at least a portion of the brominated hydrocarbon of the feed stream to chlorinated hydrocarbon.

A product stream including chlorinated hydrocarbon, optionally brominated hydrocarbon, optionally water, and optionally organic solvent is removed from an upper portion 118 of first fixed bed vessel 11 through conduit 121. The product stream is forwarded through conduit 121, through valve 124, which is positioned to direct the product stream through conduit 127 and into upper portion 133 of phase separator 130. For purposes of non-limiting illustration, when the product stream includes 1,2-dichloroethane, 1-bromo-2-chloroethane, water, and optionally organic solvent, a separated aqueous stream including water is removed from upper portion 133 of phase separator 130 through conduit 139. The separated aqueous stream is forwarded by pump 142 through conduit 145 for storage, disposal, and/or further processing (not shown). A separated organic stream including 1,2-dichloroethane, 1-bromo-2-chloroethane, and optionally organic solvent is removed from lower portion 136 of phase separator 130 through conduit 148. The separated organic stream is forwarded by pump 151 through conduit 153 for storage and/or further processing, such as separation of 1,2-dichloroethane and 1-bromo-2-chloroethane from each other (by one or more unit operations, not shown). The separated/isolated 1-bromo-2-chloroethane is, with some embodiments, forwarded (through one or more conduits, not shown) to container 100 and/or into conduit 103, and re-introduced into first fixed bed vessel 11.

In accordance with some embodiments, and with reference to FIG. 3, at least a portion of the separated organic stream (including, for example, 1,2-dichloroethane, 1-bromo-2-chloroethane, and optionally organic solvent) is passed through appropriately adjusted valve 200 and recycle conduit 203 into conduit 103, from where it passes optionally together with the feed stream (from source 100) through preheater 106, conduit 109, appropriately adjusted valve 110, conduit 112, and up through fixed bed vessel 11. One or more additional valves (not shown) and/or conduits (not shown) can be included in and/or associated with recycle conduit 203, and/or conduit 153, and/or conduit 103, in accordance with art-recognized methods.

With further non-limiting reference to FIG. 3 and in accordance with some embodiments of the present invention, first fixed bed 14, residing within first fixed bed vessel 11, includes a wet ion exchange resin that includes water in an amount of greater than 30 percent by weight, based on the total weight of the wet ion exchange resin (i.e., based on the total weight of the ion exchange resin and the water). The wet ion exchange resin is, with some embodiments, subjected to an azeotropic drying process. Azeotropic drying of the wet ion exchange resin involves, with some embodiments, forwarding liquid hydrocarbon from a source of hydrocarbon, such as residing in container 156, through conduit 159. During the azeotropic drying process, valve 110 is positioned (or turned) so as to prevent the feed stream from passing from conduit 109 through conduit 112 and up into lower portion 115 of first fixed bed vessel 11. The liquid hydrocarbon is further forwarded by pump 162 through conduit 165 and into vaporizer 168, which converts the liquid hydrocarbon to heated hydrocarbon vapor. The heated hydrocarbon vapor is forwarded through conduit 169, through valve 124, which is positioned (or turned) to direct the heated hydrocarbon vapor through conduit 121 into upper portion 118 of first fixed bed vessel 11.

With some embodiments of the present invention, the temperature of the heated hydrocarbon vapor is measured and recorded as it passes through conduit 121 by one or more thermocouples (not shown). The temperature of the heated hydrocarbon vapor as it passes through conduit 121 is, with some embodiments, from 40° C. to 150° C., or from 60° C. to 150° C., or from 80° C. to 150° C., or from 84° C. to 110° C.

Within first fixed bed vessel 11, the heated hydrocarbon vapor and the wet ion exchange resin are contacted together, which results in the formation of an azeotrope with the water of the wet ion exchange resin, which further results in the formation of a wet vapor that includes hydrocarbon vapor and water vapor. The wet vapor is removed from lower portion 115 of first fixed bed vessel 11 through conduit 112. The wet vapor is forwarded through conduit 112, through valve 110, which is position (or turned) to direct the wet vapor through conduit 171 into condenser 174, which converts the wet vapor into a wet liquid (or wet condensate) that includes liquid water and liquid hydrocarbon. The wet liquid is forwarded through conduit 177 into phase separator 130.

For purposes of non-limiting illustration with regard to the azeotropic drying process, and in accordance with some embodiments of the present invention, the hydrocarbon vapor includes 1,2-dichloroethane vapor and/or 1-bromo-2-chloroethane vapor. Correspondingly, the wet liquid/wet condensate includes liquid water, and liquid 1,2-dichloroethane and/or liquid 1-bromo-2-chloroethane, which is forwarded through conduit 177 into phase separator 130. An aqueous stream including water is removed from upper portion 133 of phase separator 130 through conduit 139, and forwarded by pump 142 through conduit 145 for storage, disposal, and/or further processing (not shown). An organic stream including liquid 1,2-dichloroethane and/or liquid 1-bromo-2-chloroethane is removed from lower portion 136 of phase separator 130 through conduit 148, and forwarded by pump 151 through conduit 153 for storage and/or further processing (not shown).

In accordance with some embodiments of the present invention, prior to conducting the azeotropic drying process, the wet ion exchange resin is analyzed to determine the water content thereof, in accordance with art-recognized methods. During the azeotropic drying process, one or more samples of the wet vapor removed from first fixed bed vessel 11, and more typically the wet liquid/condensate removed from condenser 174, is/are analyzed to determine how much water has been removed from the wet ion exchange resin. When the amount of water removed during the azeotropic drying process is at least sufficient to result in the formation of ion exchange resin including water in an amount of less than or equal to 30 percent by weight, based on the total weight of the ion exchange resin and the water, the azeotropic drying process is stopped. Subsequently, the feed stream including brominated hydrocarbon is introduced into first fixed bed vessel 11 through conduit 112, as described above.

With some embodiments of the present invention, fresh ion exchange resin, that is for example loaded into first fixed bed vessel 11, is washed/treated with aqueous HCl for purposes including, but not limited to, removing contaminants therefrom and/or ensuring that the fresh ion exchange resin includes at least a sufficient amount of chloride groups. In accordance with some further embodiments of the present invention, after converting brominated hydrocarbon to chlorinated hydrocarbon, the ion exchange resin has a reduced amount of chloride groups (because at least some of the chloride groups have been replaced with bromide groups). The ion exchange resin having a reduced amount of chloride groups is, with some embodiments, subjected to a regeneration process, which involves contacting the ion exchange resin with aqueous HCl.

The aqueous HCl, for washing and/or regeneration, can include any suitable amount of HCl. With some embodiments, the aqueous HCl includes HCl in an amount of from 0.5 percent by weight to 20 percent by weight, or from 1 percent by weight to 15 percent by weight, or from 3 percent by weight to 5 percent by weight, the percent weights in each case being based on total weight of the aqueous HCl (with the remainder including substantially water).

With reference to FIG. 3, washing/regeneration involves, with some embodiments, forwarding a source of aqueous HCl from container 180 through conduit 183 into upper portion 118 of first fixed bed vessel 11. During the HCl washing and regeneration processes, valve 110 is positioned to prevent feed passing from conduit 109 up through conduit 112 into lower portion 115 of first fixed bed vessel 11. The aqueous HCl and ion exchange resin of fixed bed 14 are contacted together within first fixed bed vessel 11, which results in an increase in the amount of chloride ions on the ion exchange resin, a decrease in the amount of bromide ions on the ion exchange resin, and the formation of an aqueous post-wash/post-regeneration stream that includes water, HBr, and optionally HCl. The aqueous post-wash/post-regeneration stream is removed from lower portion 115 of fixed bed vessel 11 through conduit 112, passes through valve 110, which is positioned/turned to direct the aqueous post-wash/post-regeneration stream through conduit 185 from where it is forward to storage, disposal, and/or further processing (not shown). With some embodiments, if the level of HCl in the aqueous post-wash/post-regeneration stream is high enough (e.g., greater than the amount of HBr therein) it can be introduced into container 180 and/or conduit 183 by one or more conduits (not shown) and thereby re-introduced into upper portion 118 of first fixed bed vessel 11.

In accordance with some embodiments of the present invention, the wet ion exchange resin including water in an amount of greater than 30 percent by weight, based on the total weight of the ion exchange resin and the water, can be dried by contact with a gas, such as by continuously passing a gas over (and/or through) the wet ion exchange resin. With some embodiments, the gas (or drying gas) used to dry the wet ion exchange resin is selected from one or more inert gasses, which do not adversely affect and/or interact with the ion exchange resin and/or residual organic materials that may be present. Classes and examples of drying gasses include, but are not limited to: noble gasses, such as argon; nitrogen; $CO_2$; air; and combinations thereof. With some further embodiments, the drying gas is heated to an elevated temperature when contacted with the wet ion exchange resin, such as a temperature of from 40° C. to 250° C., or from 60° C. to 150° C.

For purposes of non-limiting illustration and with reference to FIG. 3, a drying gas, such as nitrogen (optionally heated to an elevated temperature) is introduced into conduit 169 (from a conduit, not shown), and passes through appropriately adjusted valve 124 and conduit 121 into upper portion 118 of fixed bed vessel 11. The drying gas passes down through fixed bed vessel 11 and over the wet ion exchange resin of fixed bed 14. A wet drying gas including water (such as water vapor) is removed from lower portion 115 of fixed bed vessel 11 through conduit 112. The wet drying gas can be forwarded to further processing, such as removal of water there-from, such as through appropriately adjusted valve 110 and conduit 185, with some embodiments.

In accordance with the present invention there is provided a method of forming a dried ion exchange resin that includes providing a fixed bed vessel that includes therein a fixed bed that includes a wet ion exchange resin, wherein the wet ion exchange resin has a first amount of water.

The fixed bed vessel of the method of forming a dried ion exchange resin is, with some embodiments, as described previously herein with regard to the first fixed bed vessel.

With some embodiments, the fixed bed of the fixed bed vessel of the method of forming a dried ion exchange resin, is defined by the wet ion exchange resin or the dried ion exchange resin. The ion exchange resin, of the wet ion exchange resin and the dried ion exchange resin, can be selected from any ion exchange resin, such as, but not limited to, anion exchange resins and cation exchange resins. With some embodiments, the ion exchange resin, of the wet ion exchange resin and the dried ion exchange resin, is in each case an anion exchange resin that includes chloride groups ($Cl^-$ groups) as described previously herein with regard to the ion exchange resin of the method of converting a brominated hydrocarbon to a chlorinated hydrocarbon.

With some embodiments the ion exchange resin, of the wet ion exchange resin and the dried ion exchange resin, is selected from: gel-type ion exchange resins (e.g., having an average pore size of from 0.1 nm to 100 nm, or from 0.1 nm to 50 nm, or from 0.1 nm to 20 nm, or from 1 nm to 2 nm); macroporous-type ion exchange resins (e.g., having an average pore size of from 5 nm to 20,000 nm, or from 10 nm to 10,000 nm, or from 15 nm to 5000 nm, or from 20 nm to 100 nm), or combinations thereof. In accordance with some embodiments, the ion exchange resin of the wet ion exchange resin and the dried ion exchange resin, is selected from macroporous-type ion exchange resins. In accordance with some further embodiments of the present invention, macroporous-type ion exchange resins provide improved reaction kinetics, as compared to gel-type ion exchange resins.

The wet ion exchange resin includes a first amount of water. With some embodiments, the wet ion exchange resin includes water in an amount (i.e., a first amount of water) of greater than 0 percent by weight to less than or equal to 200 percent by weight, or greater than 0 percent by weight to less than or equal to 100 percent by weight, based on the total weight of the wet ion exchange resin (i.e., based on the total weight of the ion exchange resin and the water). With some further embodiments, the wet ion exchange resin includes water in an amount (i.e., a first amount of water) of from 5 percent by weigh to 95 percent by weight, or from 10 percent by weight to 90 percent by weight, or from 15 percent by weight to 85 percent by weight, or from 20 percent by weight to 80 percent by weight, or from 25 percent by weight to 75 percent by weight, or from 30 percent by weight to 70 percent by weight, or from 35 percent by weight to 65 percent by weight, inclusive of the recited values, and the percent weights in each case being based on total weight of the wet ion exchange resin. With some embodiments, the wet ion exchange resin includes water in an amount (i.e., a first amount of water) of greater than 30 percent by weight, such as from greater than 30 percent by weight to 200 percent by weight, or from greater than 30 percent by weight to 100 percent by weight, or from greater than 30 percent by weight to 90 percent by weight, the percent weights in each case being based on total weight of the wet ion exchange resin including the water.

The method of forming a dried ion exchange resin further includes, contacting together, within the fixed bed vessel, the wet ion exchange resin and a heated hydrocarbon vapor that forms an azeotrope with water of the wet ion exchange resin, thereby forming a wet vapor that includes hydrocarbon vapor and water vapor.

With the method of forming a dried ion exchange resin, the term "vapor" with regard to the term "hydrocarbon vapor" means the heated hydrocarbon is in a gaseous phase. The temperature of the heated hydrocarbon vapor is selected such that it is capable of forming an azeotrope with the water of the wet ion exchange resin under the pressure within the first fixed bed vessel. With some embodiments, the pressure within the fixed bed vessel during the method of forming a dried ion exchange resin is substantially ambient pressure, such as 1 atmosphere. With some embodiments, the temperature of the heated hydrocarbon vapor, when introduced into the fixed bed vessel, is from 40° C. to 150° C., or from 60° C. to 150° C., or from 80° C. to 150° C., or from 84° C. to 110° C.

As used herein, with the method of forming a dried ion exchange resin, the term "vapor" with regard to the term "water vapor" means water that is in a gaseous phase.

In accordance with some embodiments of the method of forming a dried ion exchange resin of the present invention, the heated hydrocarbon vapor is selected from non-halogen substituted hydrocarbon, halogen substituted hydrocarbon, or combinations thereof. The non-halogen substituted hydrocarbon and the halogen substituted hydrocarbon used in the method of forming a dried ion exchange resin can each be independently selected from those classes and examples described previously herein with regard to the azeotropic drying portion of the method of converting a brominated hydrocarbon to a chlorinated hydrocarbon. With some embodiments, the hydrocarbon of the heated hydrocarbon vapor is a halogen substituted hydrocarbon selected from 1,2-dichloroethane, 1-bromo-2-chloroethane, or combinations thereof.

The method of forming a dried ion exchange resin further includes, removing the wet vapor from the fixed bed vessel, thereby forming the dried ion exchange resin that includes a second amount of water, where the second amount of water (of the dried ion exchange resin) is less than the first amount of water (of the wet ion exchange resin). The wet vapor removed from the fixed bed vessel, with some embodiments, includes hydrocarbon vapor and water vapor.

The second amount of water of the dried ion exchange resin can be any amount, such as from 0 percent by weight to less than 100 percent by weight, based on the total weight of the dried ion exchange resin and the water, provided the second amount of water (of the dried ion exchange resin) is less than the first amount of water (of the wet ion exchange resin).

With some embodiments, the second amount of water is less than or equal to 30 percent by weight, based on the total weight of the dried ion exchange resin and the water. With some further embodiments, the second amount of water is from greater than or equal to 0 percent by weight to less than or equal to 30 percent by weight, or from 0.25 percent by weight to 25 percent by weight, or from 0.5 percent by weight to 20 percent by weight, or from 1 percent by weight to 15 percent by weight, or from 1.5 percent by weight to 10 percent by weight, or from 2 percent by weight to 5 percent by weight, the percent weights in each case being based on the total weight of the dried ion exchange resin and the water. With some additional embodiments, the second amount of water is from greater than or equal to 0 percent by weight to 0.25 percent by weight, or from greater than or equal to 0 percent by weight to 0.15 percent by weight, or from greater than or equal to 0 percent by weight to 0.1 percent by weight, or from greater than or equal to 0 percent by weight to 0.05 percent by weight, the percent weights in each case being based on the total weight of the dried ion exchange resin and the water.

The first amount of water (of the wet ion exchange resin) and the second amount of water (of the dried ion exchange resin) can each be determined in accordance with art-recognized methods, including, but not limited to, those methods described previously herein, such as by volumetric Karl Fischer titration and/or coulometric Karl Fischer titration.

The method of forming a dried ion exchange resin can be described with reference to FIG. 3 of the drawings in accordance with the description provided previously herein with regard to the azeotropic drying portion of the method of converting a brominated hydrocarbon to a chlorinated hydrocarbon. With reference to FIG. 3, the first fixed bed vessel 11 is the fixed bed vessel, and the first fixed bed 14 is the fixed bed, in each case, of the method of forming a dried ion exchange resin according to the present invention.

The present invention can be further characterized by one or more of the following non-limiting clauses.

Clause 1: A method of converting a brominated hydrocarbon to a chlorinated hydrocarbon comprising:
(a) providing the brominated hydrocarbon, wherein the brominated hydrocarbon comprises at least one replaceable bromo group, wherein each replaceable bromo group is independently covalently bonded to a $sp^3$ hybridized carbon;
(b) contacting together the brominated hydrocarbon and an ion exchange resin comprising chloride groups, wherein the ion exchange resin comprises water in an amount of less than or equal to 30 percent by weight, based on the total weight of the ion exchange resin and the water, thereby replacing at least one replaceable bromo group of the brominated hydrocarbon with a chloro group, and converting at least a portion of the brominated hydrocarbon to the chlorinated hydrocarbon; and
(c) isolating the chlorinated hydrocarbon from said ion exchange resin.

Clause 2: The method of clause 1 wherein, the ion exchange resin has a molar equivalents of chloride groups, said brominated hydrocarbon has a molar equivalents of replaceable bromo groups, and a ratio of said molar equivalents of chloride groups of the ion exchange resin to said molar equivalents of replaceable bromo groups of the brominated hydrocarbon is at least 0.5:1, or at least 1:1.

Clause 3: The method of clause 2 wherein, the ratio of the molar equivalents of chloride groups of the ion exchange resin to the molar equivalents of replaceable bromo groups of the brominated hydrocarbon is from 0.5:1 to 100:1, or from 0.5:1 to 10:1, or from 0.5:1 to 4:1, or from 1:1 to 4:1.

Clause 4: The method of any one of clauses 1 to 3 wherein, contacting the brominated hydrocarbon with the ion exchange resin is conducted at a temperature of at least 30° C. (or at least 50° C.), and a molar conversion of the brominated hydrocarbon to the chlorinated hydrocarbon is at least 10 percent, or at least 25 percent, or at least 30 percent, or at least 50 percent, or at least 75 percent, or at least 80 percent, or at least 90 percent, based in each case on initial moles of brominated hydrocarbon.

Clause 5: The method of any one of clauses 1 to 4 wherein, contacting together the brominated hydrocarbon and the ion exchange resin is conducted at a temperature of from 30° C. to 200° C. (or from 50° C. to 177° C.).

Clause 6: The method of any one of clauses 1 to 5 wherein, the brominated hydrocarbon is selected from the group consisting of brominated linear or branched aliphatic hydrocarbons, brominated alicyclic hydrocarbons, aromatic hydrocarbons that include at least one brominated linear or branched aliphatic hydrocarbon group and/or at least one brominated alicyclic hydrocarbon group, and combinations thereof.

Clause 7: The method of clause 6 wherein, the brominated hydrocarbon is selected from the group consisting of brominated linear or branched $C_1$-$C_{20}$ alkanes, brominated $C_3$-$C_8$ cycloalkanes, benzene having at least one brominated linear or branched $C_1$-$C_{20}$ alkyl group, and combinations thereof.

Clause 8: The method of any one of clauses 1 to 7 wherein, the brominated hydrocarbon further comprises at least one $sp^3$ hybridized carbon having at least one chloro group covalently bonded thereto, and further wherein said $sp^3$ hybridized carbon having at least one chloro group bonded thereto is the same or different than the $sp^3$ hybridized carbon having at least one replaceable bromo group bonded thereto.

Clause 9: The method of clause 8 wherein, the brominated hydrocarbon comprises 1-bromo-2-chloroethane, and the chlorinated hydrocarbon comprises 1,2-dichloroethane.

Clause 10: The method of clause 8 wherein, said brominated hydrocarbon comprises bromochloromethane, and said chlorinated hydrocarbon comprises dichloromethane.

Clause 11: The method of any one of clauses 1 to 10 wherein, the ion exchange resin comprises water in an amount of from 1 percent by weight to 10 percent by weight, based on total weight of the ion exchange resin.

Clause 12: The method of clause 11 wherein, contacting together the brominated hydrocarbon and the ion exchange resin is conducted in the presence of an organic solvent, the organic solvent being selected from the group consisting of hydrocarbons, chlorinated hydrocarbons that are free of bromo groups, and combinations thereof.

Clause 13: A method of converting a brominated hydrocarbon to a chlorinated hydrocarbon comprising:
 (a) providing a feed stream comprising the brominated hydrocarbon, wherein the brominated hydrocarbon comprises at least one replaceable bromo group, wherein each replaceable bromo group is independently covalently bonded to a $sp^3$ hybridized carbon;
 (b) providing a first fixed bed vessel comprising a first fixed bed comprising an ion exchange resin comprising chloride groups, wherein the ion exchange resin comprises water in an amount of less than or equal to 30 percent by weight, based on the total weight of the ion exchange resin and the water;
 (c) introducing the feed stream into the first fixed bed vessel, and contacting together within the first fixed bed vessel the brominated hydrocarbon and the ion exchange resin, thereby replacing at least one replaceable bromo group of the brominated hydrocarbon with a chloro group, and converting at least a portion of the brominated hydrocarbon to the chlorinated hydrocarbon; and
 (d) withdrawing a product stream from the first fixed bed vessel, wherein the product stream comprises the chlorinated hydrocarbon.

Clause 14: The method of clause 13 wherein, at least a portion of the product stream is introduced into the first fixed bed vessel.

Clause 15: The method of clauses 13 or 14 further comprising,
 providing a second fixed bed vessel comprising a second fixed bed comprising a drying agent,
 introducing at least a portion of the product stream into the second fixed bed vessel, thereby removing at least a portion of residual water from the product stream, and forming a dried product stream, and
 removing the dried product stream from the second fixed bed vessel.

Clause 16: The method of clause 15, wherein the drying agent is selected from $CaCl_2$, alumina, silica, molecular sieves, and combinations thereof.

Clause 17: The method of clause 15 further comprising, introducing at least a portion of the dried product stream into the first fixed bed vessel.

Clause 18: The method of any one of clauses 13 to 17 wherein,
 the ion exchange resin of said first fixed bed has a molar equivalents of chloride groups,
 the first fixed bed vessel comprising the first fixed bed has a maximum static feed volume,
 a volume of the feed stream that is equivalent to the maximum static feed volume provides a maximum static molar equivalents of replaceable bromo groups, and
 a ratio of the molar equivalents of chloride groups of the ion exchange resin to the maximum static molar equivalents of replaceable bromo groups is at least 0.5:1, or at least 1:1.

Clause 19: The method of clause 18 wherein, the ratio of the molar equivalents of chloride groups of the ion exchange resin to the maximum static molar equivalents of replaceable bromo groups is from 0.5:1 to 100:1, or from 0.5:1 to 10:1, or from 0.5:1 to 4:1, or from 1:1 to 4:1.

Clause 20: The method of any one of clauses 13 to 19 wherein, contacting together within the first fixed bed vessel the brominated hydrocarbon and the ion exchange resin, is conducted at a temperature of at least 30° C. (or at least 50° C.), and a molar conversion of the brominated hydrocarbon to the chlorinated hydrocarbon is at least 10 percent, or at least 25 percent, or at least 30 percent, or at least 50 percent, or at least 75 percent, or at least 80 percent, or at least 90 percent, based in each case on total moles of brominated hydrocarbon passed through the first fixed bed vessel.

Clause 21: The method of any one of clauses 13 to 20 wherein, contacting together within the first fixed bed vessel the brominated hydrocarbon and the ion exchange resin, is conducted at a temperature of from 30° C. to 200° C. (or from 50° C. to 177° C.).

Clause 22: The method of clause 13 wherein,
 said first fixed bed comprises a wet ion exchange resin comprising water in an amount of greater than 30 percent by weight, based on the total weight of said wet ion exchange resin and the water,
 said method further comprising converting said wet ion exchange resin to said ion exchange resin comprising water in an amount of less than or equal to 30 percent by weight, based on the total weight of said ion exchange resin and the water, by subjecting said wet ion exchange resin to an azeotropic drying process, wherein said azeotropic drying process comprises,
 contacting together, within said first fixed bed vessel, said wet ion exchange resin and a heated hydrocarbon vapor that forms an azeotrope with water of said wet ion exchange resin, thereby forming a wet vapor comprising hydrocarbon vapor and water vapor, and
 removing said wet vapor from said first fixed bed vessel, thereby forming said ion exchange resin comprising water in an amount of less than or equal to 30 percent by weight, based on the total weight of said ion exchange resin and the water.

Clause 23: The method of clause 22 wherein, said azeotropic drying process is conducted prior to introducing said feed stream into said first fixed bed vessel.

Clause 24: The method of clauses 22 or 23 wherein, the hydrocarbon of said heated hydrocarbon vapor is selected from the group consisting of non-halogen substituted hydrocarbon, halogen substituted hydrocarbon, and combinations thereof.

Clause 25: The method of clause 24 wherein, the halogen substituted hydrocarbon is selected from the group consisting of chloro substituted hydrocarbon, bromo substituted hydrocarbon, chloro and bromo substituted hydrocarbon, and combinations thereof.

Clause 26: The method of clause 25 wherein, the halogen substituted hydrocarbon is selected from the group consisting of 1,2-dichloroethane, 1-bromo-2-chloroethane, and combinations thereof.

Clause 27: The method of any one of clauses 22 to 26 wherein, the heated hydrocarbon vapor has a temperature of from 40° C. to 150° C., or from 60° C. to 150° C., or from 80° C. to 150° C., or from 84° C. to 110° C.

Clause 28: The method of any one of clauses 22 to 27 wherein, the wet ion exchange resin includes water in an amount of greater than 30 percent by weight and less than or equal to 90 percent by weight, the percent weights in each case being based on total weight of the wet ion exchange resin.

Clause 29: A method of forming a dried ion exchange resin comprising:
(a) providing a fixed bed vessel comprising a fixed bed comprising a wet ion exchange resin, wherein said wet ion exchange resin comprises a first amount of water;
(b) contacting together, within said fixed bed vessel, said wet ion exchange resin and a heated hydrocarbon vapor that forms an azeotrope with water of said wet ion exchange resin, thereby forming a wet vapor comprising hydrocarbon vapor and water vapor; and
(c) removing said wet vapor from said fixed bed vessel, thereby forming said dried ion exchange resin comprising a second amount of water, wherein said second amount of water is less than said first amount of water.

Clause 30: The method of clause 29 wherein,
said first amount of water is greater than 30 percent by weight, based on the total weight of said wet ion exchange resin including the water, and
said second amount of water is less than or equal to 30 percent by weight, based on the total weight of said dried ion exchange resin and the water.

Clause 31: The method of clauses 29 or 30 wherein, the hydrocarbon of said heated hydrocarbon vapor is selected from the group consisting of non-halogen substituted hydrocarbon, halogen substituted hydrocarbon, and combinations thereof.

Clause 32: The method of clause 31 wherein, the halogen substituted hydrocarbon is selected from the group consisting of chloro substituted hydrocarbon, bromo substituted hydrocarbon, chloro and bromo substituted hydrocarbon, and combinations thereof.

Clause 33: The method of clause 32 wherein, the halogen substituted hydrocarbon is selected from the group consisting of 1,2-dichloroethane, 1-bromo-2-chloroethane, and combinations thereof.

Clause 34: The method of any one of clauses 29 to 33 wherein, the heated hydrocarbon vapor has a temperature of from 40° C. to 150° C., or from 60° C. to 150° C., or from 80° C. to 150° C., or from 84° C. to 110° C.

The present invention is more particularly described in the example that follows, which is intended to be illustrative only, since numerous modifications and variations therein will be apparent to those skilled in the art.

EXAMPLES

Example 1

The conversion of 1-bromo-n-butane to 1-chloro-n-butane in accordance with the present invention was conducted as follows.

A 250 mL (milliliters) three-necked round-bottom flask equipped with a magnetic stir bar, internal thermocouple coupled to an external and underlying heating mantle, condenser, and nitrogen sweep was used in this example. To the flask was added 8.73 grams of dried chlorinated anion exchange resin, having: a water content of 3 percent by weight, based on total weight of the chlorinated anion exchange resin; and a total chloride content of 32.5 mmoles (milli-moles or millimoles). The chlorinated anion exchange resin was Purolite PPA 500PLUS chlorinated anion exchange resin, which, as received, initially had a water content of 54 percent by weight. The initial or wet Purolite PPA 500PLUS chlorinated anion exchange resin was washed with methanol and then subjected to reduced pressure until a constant weight was measured, at which point it was determined to have a water content of 3 percent by weight.

To the flask was also added 100.67 grams of an organic composition containing 3.9 percent by weight of 1-bromo-n-butane (28.81 mmoles), and 96.1 percent by weight of tetrachloroethylene, the percent weights being based on the total weight of organic composition. A sample of the organic composition was analyzed by gas chromatography prior to addition to the flask.

The contents of the flask were heated from 25° C. to 90° C. over a period of 15 minutes with continuous agitation provided by the magnetic stir bar, and under a continuous nitrogen sweep. The contents of the flask were held at 90° C. for 24 hours with continuous agitation provided by the magnetic stir bar, and under a continuous nitrogen sweep, during which time samples were taken at 0, 1, 2, 3, 20, and 24 hours and analyzed by gas chromatography for the percent by area of 1-bromo-n-butane remaining, and the percent by area of 1-chloro-n-butane formed. The results of the gas chromatography analysis are summarized in the following Table 1, in which the term "Bromobutane" means 1-bromo-n-butane, and the term "Chlorobutane" means 1-chloro-n-butane.

TABLE 1

| Hours at 90° C. | Area % Bromobutane in Solution | Area % Chlorobutane in Solution | % Bromobutane Remaining[a] |
|---|---|---|---|
| 0 | 4.193 | 0.017 | 100 |
| 1 | 0.582 | 3.174 | 13.9 |
| 2 | 0.428 | 3.220 | 10.2 |
| 3 | 0.401 | 3.152 | 9.6 |
| 20 | 0.343 | 2.816 | 8.2 |
| 24 | 0.336 | 2.780 | 8.0 |

[a]Determined by gas chromatography using the following formula: 100 − [{(Area % Initial bromobutane − Area % bromobutane in Sample)/(Area % Initial bromobutane)} × 100]

Example 2

The conversion of 1-bromo-2-chloroethane to 1,2-dichloroethane in accordance with the present invention was conducted as follows.

A 250 mL three-necked round-bottomed flask equipped with a magnetic stir bar, internal thermocouple coupled to an external and underlying heating mantle, condenser, and nitrogen sweep was used in this example. To the flask was added 14.36 grams of dried chlorinated anion exchange resin, having: a water content of 3 percent by weight, based on the total weight of the chlorinated anion exchange resin and the water; and a total chloride content of 54.5 mmoles. The chlorinated anion exchange resin was Purolite PPA500PLUS chlorinated anion exchange resin, which, as received, initially had a water content of 54 percent by weight. The initial or wet Purolite PPA 500PLUS chlorinated anion exchange resin was washed with methanol and then subjected to reduced pressure until a constant weight was measured, at which point it was determined to have a water content of 3 percent by weight.

To the flask was also added 74.7 grams of an organic composition containing 4.39 percent by weight of 1-bromo-2-chloroethane (22.87 mmoles), 73.78 percent by weight of tetrachloroethylene, and 21.82 percent by weight of 1,1,2-trichloroethane, the percent weights being based on the total weight of organic composition. A sample of the organic composition was analyzed by gas chromatography prior to addition to the flask.

The contents of the flask were heated from 20° C. to 90° C. over a period of 15 minutes with continuous agitation provided by the magnetic stir bar, and under a continuous nitrogen sweep. The contents of the flask were held at 90° C. for 22 hours with continuous agitation provided by the magnetic stir bar, and under a continuous nitrogen sweep, during which time samples were taken at 0, 1, 2, 3, and 22 hours and analyzed by gas chromatography for the percent by area of 1-bromo-2-chloroethane remaining, and the percent by area of 1,2-dichloroethane formed. The results of the gas chromatography analysis are summarized in the following Table 2.

TABLE 2

| Hours at 90° C. | Area % 1-Bromo-2-Chloroethane in Solution | Area % 1,2-Dichloroethane in Solution | % 1-Bromo-2-Chloroethane Remaining[b] |
|---|---|---|---|
| 0 | 3.88 | 0 | 100 |
| 1 | 0.10 | 3.39 | 2.58 |
| 2 | 0.08 | 3.45 | 2.06 |
| 3 | 0.07 | 3.39 | 1.80 |
| 22 | 0.06 | 3.50 | 1.55 |

[b]Determined by gas chromatography using the following formula: 100 − [{(Area % Initial 1-bromo-2-chloroethane − Area % 1-bromo-2-chloroethane in Sample)/(Area % Initial 1-bromo-2-chloroethane)} × 100]

Comparative Example

The conversion of 1-bromo-2-chloroethane to 1,2-dichloroethane using a chlorinated anion exchange resin having a content of water of 54 percent by weight, based on total weight of the chlorinated anion exchange resin, was conducted as follows.

A 250 mL three-necked round-bottomed flask equipped with a magnetic stir bar, internal thermocouple coupled to an external and underlying heating mantle, condenser, and nitrogen sweep was used in this example. To the flask was added 34.97 grams of as-received Purolite PPA500PLUS chlorinated anion exchange resin, having: an as-received water content of 54 percent by weight, based on the total weight of the chlorinated anion exchange resin and the water; and a total chloride content of 59.95 mmoles.

To the flask was also added 74.4 grams of an organic composition containing 4.39 percent by weight of 1-bromo-2-chloroethane (22.77 mmoles), 73.78 percent by weight of tetrachloroethylene, and 21.82 percent by weight of 1,1,2-trichloroethane, the percent weights being based on the total weight of organic composition. A sample of the organic composition was analyzed by gas chromatography prior to addition to the flask.

The contents of the flask were heated from 20° C. to 86° C. (reflux) over a period of 19 minutes with continuous agitation provided by the magnetic stir bar, and under a continuous nitrogen sweep. The contents of the flask were held at 86° C. (reflux) for 22 hours with continuous agitation provided by the magnetic stir bar, and under a continuous nitrogen sweep, during which time samples were taken at 0, 1, 2, 4, 6, and 22 hours and analyzed by gas chromatography for the percent by area of 1-bromo-2-chloroethane remaining, and the percent by area of 1,2-dichloroethane formed. During the course of maintaining the contents of the flask at 86° C. for 22 hours, there was observed the condensation of water on interior surfaces of the flask (above the surface of the reaction mixture). It was hypothesized that the observed condensation of water contributed to the conversion of 1-bromo-2-chloroethane to 1,2-dichloroethane to proceed to an extent further than was expected. The results of the gas chromatography analysis are summarized in the following Table 3.

TABLE 3

| Hours at 86° C. | Area % 1-Bromo-2-Chloroethane in Solution | Area % 1,2-Dichloroethane in Solution | % 1-Bromo-2-Chloroethane Remaining[c] |
|---|---|---|---|
| 0 | 3.88 | 0 | 100 |
| 1 | 3.65 | 0.15 | 94.07 |
| 2 | 3.43 | 0.29 | 88.40 |
| 4 | 3.06 | 0.52 | 78.87 |
| 6 | 2.84 | 0.77 | 73.20 |
| 22 | 1.41 | 2.10 | 36.34 |

[c]Determined by gas chromatography using the following formula: 100 − [{(Area % Initial 1-bromo-2-chloroethane − Area % 1-bromo-2-chloroethane in Sample)/(Area % Initial 1-bromo-2-chloroethane)} × 100]

The results of the above examples demonstrate that the conversion of brominated hydrocarbon to chlorinated hydrocarbon in accordance with the present invention, such as represented by Examples 1 and 2, can be achieved with a desirably and unexpectedly high level of conversion (92.0% and 98.5% conversion), as compared to a comparative process, such as represented by the Comparative Example (63.7% conversion), under similar reaction conditions including temperature and time.

Example 3

The conversion of bromochloromethane to dichloromethane in accordance with the present invention was conducted as follows.

A 250 mL three-necked round-bottomed flask equipped with a magnetic stir bar, internal thermocouple coupled to an external and underlying heating mantle, condenser, and nitrogen sweep was used in this example. To the flask was added 19.71 grams of dried chlorinated anion exchange resin, having: a water content of 3 percent by weight, based on the total weight of the chlorinated anion exchange resin and the water; and a total chloride content of 74.8 mmoles. The chlorinated anion exchange resin was Purolite PPA500PLUS chlorinated anion exchange resin, which, as received, initially had a water content of 54 percent by weight. The initial or wet Purolite PPA 500PLUS chlorinated anion exchange resin was washed with methanol and then subjected to a stream of nitrogen gas until a constant weight was measured, at which point it was determined to have a water content of 3 percent by weight.

To the flask was also added 89.62 grams of an organic composition containing 6.91 percent by weight of bromochloromethane (48.85 mmoles) and 93.09 percent by weight of chloroform, the percent weights being based on the total weight of organic composition. A sample of the organic composition was analyzed by gas chromatography prior to addition to the flask.

The contents of the flask were heated from 20° C. to 63° C. over a period of 12 minutes with continuous agitation provided by the magnetic stir bar, and under a continuous nitrogen sweep. The contents of the flask were held at 60-63° C. for 24 hours with continuous agitation provided by the magnetic stir bar, and under a continuous nitrogen sweep, during which time samples were taken at 2, 4, 6, and 24 hours and analyzed by gas chromatography for the percent by area of bromochloromethane remaining, and the percent by area of dichloromethane formed. The results of the gas chromatography analysis are summarized in the following Table 4.

TABLE 4

| Hours at 90° C. | Area % Bromo-chloromethane in Solution | Area % Dichloromethane in Solution | % Bromo-chloromethane Remaining[d] |
|---|---|---|---|
| 0 | 8.57 | 0 | 100 |
| 2 | 5.80 | 2.35 | 67.68 |
| 4 | 4.17 | 3.02 | 48.66 |
| 6 | 3.16 | 2.76 | 36.87 |
| 24 | 0.46 | 2.96 | 5.37 |

[d]Determined by gas chromatography using the following formula: 100 − [{(Area % Initial bromochloromethane − Area % bromochloromethane in Sample)/(Area % Initial bromochloromethane)} × 100]

The results of the above Example 3 demonstrate that the conversion of a brominated hydrocarbon, in this case bromochloromethane, to a chlorinated hydrocarbon, in this case dichloromethane, in accordance with the present invention, can be achieved with a desirably and unexpectedly high level of conversion (such as, 94.6% conversion).

Example 4

The conversion of 1-bromo-2-chloroethane to 1,2-dichloroethane, in accordance with the present invention, using a glass column containing a chlorinated ion exchange resin was conducted as follows.

A glass column having an internal volume of about 480 mL was obtained commercially from Ace Glass (part number 5820-104; 450 mm long; internal diameter of 37 mm). To the glass column was added 303.3 grams of Purolite PPA500PLUS chlorinated anion exchange resin (having a volume of about 470 mL). The chlorinated anion exchange resin as added to the glass column included: 54 percent by weight of water, based on total weight thereof; and 18.43 grams of Cl (519.94 mmol Cl). The chlorinated anion exchange resin was dried within the glass column by, passing 500 sccm (standard cubic centimeters per minute) nitrogen gas down through the column over a period of 18 hours, while an external heating blanket, set at 100° C., was wrapped around the exterior of the glass column.

With the temperature of the external heating blanket set and maintained at 60° C., 1143.5 grams of a feed mixture composed of 1-bromo-2-chloroethane (361.84 mmol), tetrachloroethylene, and 1,1,2-trichloroethane, was fed (pumped) continuously up through the glass column over a period of 120.4 hours, which provided a one-pass residence time in the glass column of 48 hours. Five separate samples were taken from the top of the glass column and analyzed as summarized in the following Table 5. An initial sample of the feed mixture was taken (prior to being fed into the bottom of the glass column) and analyzed by gas chromatography.

TABLE 5

| Sample No. | Temperature[1] (° C.) | Time (hours) | 1-bromo-2-chloroethane Reduction (%)[2] |
|---|---|---|---|
| 1 | 60 | 53 | 91.6 |
| 2 | 60 | 67 | 92.0 |
| 3 | 60 | 75 | 90.5 |
| 4 | 60 | 99 | 89.6 |
| 5 | 60 | 118 | 89.6 |

[1]The temperature at which the external heating blanket (wrapped around the glass column) was set. [2]Reduction of 1-bromo-2-chloroethane was determined by gas chromatography using the following formula: {(Area % Initial 1-bromo-2-chloroethane − Area % 1-bromo-2-chloroethane in Sample)/(Area % Initial 1-bromo-2-chloroethane)} × 100

The product stream emerging from the top of the glass column was collected in tow over 120.4 hours (aside from the 5 separate samples as summarized in Table 4) and analyzed by gas chromatography, and it was determined (using the above equation) that 90.4 percent by area of the 1-bromo-2-chloroethane in the original feed sample had been converted to 1,2-dichloroethane. The in tow collected product stream was also found to contain 116 ppm of water (as determined by coulometric Karl Fischer titration analysis).

The results of the above Example 4 demonstrate that the conversion of brominated hydrocarbon to chlorinated hydrocarbon, in accordance with the present invention, using a fixed bed vessel (or column) that includes a fixed bed including chlorinated anion exchange resin (having a water content of less than or equal to 30 percent by weight, such as 3 to 10 percent by weight, based on total weight) can be achieved with a desirably and unexpectedly high level of conversion, such as 90.4 percent by weight.

Example 5

The conversion of 1-bromo-2-chloroethane to 1,2-dichloroethane, in accordance with the present invention, using a glass column containing a chlorinated ion exchange resin, in conjunction with multiple acid washing/regeneration and drying cycles, was conducted as follows.

A glass column having an internal volume of about 480 mL was obtained commercially from Ace Glass (part number 5820-104; 450 mm long; internal diameter of 37 mm). To the glass column was added 305 grams of Purolite PPA500PLUS chlorinated anion exchange resin (having a volume of about 470 mL). The chlorinated anion exchange resin as added to the glass column included: 54 percent by weight of water, based on total weight thereof; and 522.86 mmol Cl.

(A) Acid Washing/Regeneration Step:

Two liters of 2 molar HCl was passed down through the glass column containing the chlorinated anion exchange resin, over a period of 4 hours.

(B) Drying Step:

The acid washed/regenerated and wet chlorinated anion exchange resin was dried within the glass column by passing continuously nitrogen gas preheated to 60° C. through the glass column for 15 hours (while an external heating blanket set at 70° C. was wrapped around the glass column).

(C) Conversion of Brominated to Chlorinated Hydrocarbon Step:

After completion of the drying step, the temperature of the heating blanket was raised to 105° C. When the external temperature of the glass column was measured to be 105° C., the glass column was held at 105° C. for one hour, for purposes of equilibrating the temperature of the glass column and the anion exchange resin. After equilibration, the heating blanket was maintained at 105° C.

With the temperature of the external heating blanket set and maintained at 105° C., 1145 grams of a feed mixture composed of 1-bromo-2-chloroethane (950.11 mmol), tetrachloroethylene, and 1,1,2-trichloroethane, was fed (pumped) continuously up through the glass column at the feed rates (g/minute) shown in Table 6 below. About 460 to 470 mL of product was collected from the top of the glass column and analyzed by gas chromatography to determine percent conversion of 1-bromo-2-chloroethane to 1,2-dichloroethane, as summarized in Table 6 below.

(D) Column Cooling and Draining Step:

The heating blanket was turned off. When the temperature of the glass column was determined to be below 50° C., residual liquid was drained out of the glass column by passing nitrogen gas through the glass column.

With the glass column drained of residual liquid, the above-summarized steps (A) through (D) were repeated. In all, 15 separate (A) through (D) cycles were performed as described above using the chlorinated anion exchange resin as originally introduced into the glass column. The results of the 15 separate cycles are summarized in the following Table 6.

TABLE 6

| Cycle | Initial 1-bromo-2-chloroethane (wt %)[3] | Feed Rate, (g/min) | Conversion (Area %)[4] |
| --- | --- | --- | --- |
| 1  | 11.9 | 9.10 | 77.75 |
| 2  | 11.9 | 7.75 | 74.87 |
| 3  | 11.9 | 7.53 | 77.18 |
| 4  | 11.9 | 7.53 | 75.86 |
| 5  | 11.9 | 6.59 | 81.18 |
| 6  | 11.9 | 7.48 | 78.57 |
| 7  | 11.9 | 7.41 | 76.43 |
| 8  | 11.9 | 7.56 | 74.29 |
| 9  | 11.9 | 7.44 | 73.12 |
| 10 | 11.9 | 7.34 | 75.41 |
| 11 | 11.9 | 7.32 | 75.11 |
| 12 | 11.9 | 7.42 | 77.71 |
| 13 | 11.9 | 7.40 | 74.64 |
| 14 | 11.9 | 7.25 | 80.91 |
| 15 | 11.9 | 7.14 | 81.83 |

[3]Corresponding to the percent by area of 1-bromo-2-chloroethane present in the feed mixture, based on the total area of the feed mixture, as determined by gas chromatography.
[4]Area percent conversion of 1-bromo-2-chloroethane to 1,2-dichloroethane, as determined by gas chromatography using the following formula: {(Area % Initial 1-bromo-2-chloroethane − Area % 1-bromo-2-chloroethane in Sample)/(Area % Initial 1-bromo-2-chloroethane)} × 100

The results of the above Example 5 demonstrate that the conversion of brominated hydrocarbon to chlorinated hydrocarbon, in accordance with the present invention, can be conducted using the same initially charged anion exchange resin, in conjunction with multiple acid washing/regeneration and drying cycles.

Example 6

The formation of a dried ion exchange resin by azeotropic drying of a wet ion exchange resin, in accordance with the present invention, was conducted as follows.

A glass column having an internal volume of about 480 mL was obtained commercially from Ace Glass (part number 5820-104; 450 mm long; internal diameter of 37 mm). To the glass column was added 303.3 g of as-received Purolite PPA500Plus(Cl) ion exchange resin (having a volume of about 470 mL; and containing about 163.8 g of water, corresponding to 54 percent by weight of water, based on total weight of the ion exchange resin). Two liters of 1 molar HCl was passed down through ion exchange resin within the glass column. After completion of the HCl washing step and prior to azeotropic drying, a stream of nitrogen gas was passed through the glass column to remove bulk liquid from the ion exchange resin.

A vaporizer apparatus was positioned in-line in a feed conduit between a pump and an inlet positioned at a lower portion of the glass column. An external heating blanket was wrapped around the exterior of the glass column and set at 90° C., for purposes including minimizing or preventing the formation of condensation within the glass column. An outlet conduit was positioned at an upper portion of the glass column. The positioning of the inlet and the outlet provided for an up-flow of vapor through the ion exchange resin within the glass column.

In a first stage, over a period of two hours, 1111.7 g of wet 1,2-dichloroethane (containing 1276 ppm of water, as determined by coulometric Karl Fischer titration) was fed continuously up through the glass column as a vapor having a temperature of 86° C. to 89° C. A total of 43.44 g of water was removed and collected from the glass column during the first stage of the azeotropic drying process.

In a second sequential and subsequent stage, over a period of 4.25 hours, 2471.3 g (about 2 liters) of anhydrous 1,2-dichloroethane (obtained commercially from MilliporeSigma) was fed continuously up through the glass column as a vapor having a temperature of 88° C. to 105° C. A total of 75.32 g of water was removed and collected from the glass column during the second stage of the azeotropic drying process.

In a third sequential and subsequent stage, over a period of 7.5 hours, 2236.7 g of recycled 1,2-dichloroethane (containing 1809 ppm of water, as determined by coulometric Karl Fischer titration) was fed continuously up through the glass column as a vapor having a temperature of 92° C. to 100° C. A total of 26.30 g of water was removed and collected from the glass column during the third stage of the azeotropic drying process.

In a fourth sequential, subsequent, and final stage, over a period of 3.5 hours, 2,127.2 g of anhydrous 1,2-dichloroethane (obtained commercially from MilliporeSigma) was fed continuously up through the glass column as a vapor having a temperature of 87° C. to 104° C. A total of 1.50 g of water was removed and collected from the glass column during this fourth stage of the azeotropic drying process. The 1,2-dichloroethane collected from the top of the glass column at the conclusion of the fourth stage was determined (by coulometric Karl Fischer titration) to contain 894 ppm of water.

From all four azeotropic drying stages, a total of 146.56 g of water was removed and collected from the glass column, using a total of 7946.9 g (about 6.36 liters) of 1,2-dichloroethane vapor.

The present invention has been described with reference to specific details of particular embodiments thereof. However, it is not intended that such details be regarded as limitations upon the scope of the invention except insofar as and to the extent that they are included in the accompanying claims.

What is claimed is:

1. A method of converting a brominated hydrocarbon to a chlorinated hydrocarbon comprising:
   (a) providing said brominated hydrocarbon, wherein said brominated hydrocarbon comprises at least one replaceable bromo group, wherein each replaceable bromo group is independently covalently bonded to a $sp^3$ hybridized carbon;
   (b) contacting together said brominated hydrocarbon and an ion exchange resin comprising chloride groups, wherein said ion exchange resin comprises water in an amount of less than or equal to 30 percent by weight, based on the total weight of said ion exchange resin and water, thereby replacing at least one replaceable bromo group of said brominated hydrocarbon with a chloro group, and converting at least a portion of said brominated hydrocarbon to said chlorinated hydrocarbon; and
   (c) isolating said chlorinated hydrocarbon from said ion exchange resin.

2. The method of claim 1, said ion exchange resin has a molar equivalents of chloride groups, said brominated hydrocarbon has a molar equivalents of replaceable bromo groups, and a ratio of said molar equivalents of chloride groups of said ion exchange resin to said molar equivalents of replaceable bromo groups of said brominated hydrocarbon is at least 0.5:1.

3. The method of claim 2 wherein, said ratio of said molar equivalents of chloride groups of said ion exchange resin to said molar equivalents of replaceable bromo groups of said brominated hydrocarbon is from 0.5:1 to 100:1.

4. The method of claim 1 wherein, contacting said brominated hydrocarbon with said ion exchange resin is conducted at a temperature of at least 30° C., and a molar conversion of said brominated hydrocarbon to said chlorinated hydrocarbon is at least 30 percent, based on initial moles of brominated hydrocarbon.

5. The method of claim 4 wherein, contacting together said brominated hydrocarbon and said ion exchange resin is conducted at a temperature of from 30° C. to 200° C.

6. The method of claim 1 wherein, said brominated hydrocarbon is selected from the group consisting of brominated linear or branched aliphatic hydrocarbons, brominated alicyclic hydrocarbons, aromatic hydrocarbons that include at least one brominated linear or branched aliphatic hydrocarbon group and/or at least one brominated alicyclic hydrocarbon group, and combinations thereof.

7. The method of claim 6 wherein, said brominated hydrocarbon is selected from the group consisting of brominated linear or branched $C_1$-$C_{20}$ alkanes, brominated $C_3$-$C_8$ cycloalkanes, benzene having at least one brominated linear or branched $C_1$-$C_{20}$ alkyl group, and combinations thereof.

8. The method of claim 1 wherein, said brominated hydrocarbon further comprises at least one $sp^3$ hybridized carbon having at least one chloro group covalently bonded thereto, and further wherein said $sp^3$ hybridized carbon having at least one chloro group bonded thereto is the same or different than the $sp^3$ hybridized carbon having at least one replaceable bromo group bonded thereto.

9. The method of claim 8 wherein, said brominated hydrocarbon comprises 1-bromo-2-chloroethane, and said chlorinated hydrocarbon comprises 1,2-dichloroethane.

10. The method of claim 8 wherein, said brominated hydrocarbon comprises bromochloromethane, and said chlorinated hydrocarbon comprises dichloromethane.

11. The method of claim 1 wherein, said ion exchange resin comprises water in an amount of from 1 percent by weight to 10 percent by weight, based on total weight of the ion exchange resin and water.

12. The method of claim 11 wherein, contacting together said brominated hydrocarbon and said ion exchange resin is conducted in the presence of an organic solvent, said organic solvent being selected from the group consisting of hydrocarbons, chlorinated hydrocarbons that are free of bromo groups, and combinations thereof.

13. A method of converting a brominated hydrocarbon to a chlorinated hydrocarbon comprising:
   (a) providing a feed stream comprising said brominated hydrocarbon, wherein said brominated hydrocarbon comprises at least one replaceable bromo group, wherein each replaceable bromo group is independently covalently bonded to an $sp^3$ hybridized carbon;
   (b) providing a first fixed bed vessel comprising a first fixed bed comprising an ion exchange resin comprising chloride groups, wherein said ion exchange resin comprises water in an amount of less than or equal to 30 percent by weight, based on the total weight of said ion exchange resin and water;
   (c) introducing said feed stream into said first fixed bed vessel, and contacting together within said first fixed bed vessel said brominated hydrocarbon and said ion exchange resin, thereby replacing at least one replaceable bromo group of said brominated hydrocarbon with a chloro group, and converting at least a portion of said brominated hydrocarbon to said chlorinated hydrocarbon; and
   (d) withdrawing a product stream from said first fixed bed vessel, wherein said product stream comprises said chlorinated hydrocarbon.

14. The method of claim 13 wherein, at least a portion of said product stream is introduced into said first fixed bed vessel.

15. The method of claim 13 further comprising,
   providing a second fixed bed vessel comprising a second fixed bed comprising a drying agent,
   introducing at least a portion of said product stream into said second fixed bed vessel, thereby removing at least a portion of residual water from said product stream, and forming a dried product stream, and
   removing said dried product stream from said second fixed bed vessel.

16. The method of claim 15, wherein said drying agent is selected from $CaCl_2$, alumina, silica, molecular sieves, and combinations thereof.

17. The method of claim 13 wherein,
   said ion exchange resin of said first fixed bed has a molar equivalents of chloride groups,
   said first fixed bed vessel comprising said first fixed bed has a maximum static feed volume,
   a volume of said feed stream that is equivalent to said maximum static feed volume provides a maximum static molar equivalents of replaceable bromo groups, and
   a ratio of said molar equivalents of chloride groups of said ion exchange resin to said maximum static molar equivalents of replaceable bromo groups is at least 0.5:1.

18. The method of claim 17 wherein, said ratio of said molar equivalents of chloride groups of said ion exchange resin to said maximum static molar equivalents of replaceable bromo groups is from 0.5:1 to 100:1.

19. The method of claim 13 wherein, contacting together within said first fixed bed vessel said brominated hydrocarbon and said ion exchange resin, is conducted at a temperature of at least 30° C., and a molar conversion of said brominated hydrocarbon to said chlorinated hydrocarbon is at least 30 percent, based on total moles of brominated hydrocarbon passed through said first fixed bed vessel.

20. The method of claim 19 wherein, contacting together within said first fixed bed vessel said brominated hydrocarbon and said ion exchange resin, is conducted at a temperature of from 30° C. to 200° C.

21. The method of claim 13 wherein,
said first fixed bed comprises a wet ion exchange resin comprising water in an amount of greater than 30 percent by weight, based on the total weight of said wet ion exchange resin and water,
said method further comprising converting said wet ion exchange resin to said ion exchange resin comprising water in an amount of less than or equal to 30 percent by weight, based on the total weight of said ion exchange resin and water, by subjecting said wet ion exchange resin to an azeotropic drying process, wherein said azeotropic drying process comprises,
contacting together, within said first fixed bed vessel, said wet ion exchange resin and a heated hydrocarbon vapor that forms an azeotrope with water of said wet ion exchange resin, thereby forming a wet vapor comprising hydrocarbon vapor and water vapor, and
removing said wet vapor from said first fixed bed vessel, thereby forming said ion exchange resin comprising water in an amount of less than or equal to 30 percent by weight, based on the total weight of said ion exchange resin and water.

22. The method of claim 21 wherein, said azeotropic drying process is conducted prior to introducing said feed stream into said first fixed bed vessel.

23. The method of claim 21 wherein, the hydrocarbon of said heated hydrocarbon vapor is selected from the group consisting of non-halogen substituted hydrocarbon, halogen substituted hydrocarbon, and combinations thereof.

24. A method of forming a dried ion exchange resin comprising:
(a) providing a fixed bed vessel comprising a fixed bed comprising a wet ion exchange resin, wherein said wet ion exchange resin comprises a first amount of water;
(b) contacting together, within said fixed bed vessel, said wet ion exchange resin and a heated hydrocarbon vapor that forms an azeotrope with water of said wet ion exchange resin, thereby forming a wet vapor comprising hydrocarbon vapor and water vapor; and
(c) removing said wet vapor from said fixed bed vessel, thereby forming said dried ion exchange resin comprising a second amount of water, wherein said second amount of water is less than said first amount of water.

* * * * *